(12) United States Patent
Goletz et al.

(10) Patent No.: US 9,217,038 B2
(45) Date of Patent: Dec. 22, 2015

(54) MUC1 ANTIBODIES

(75) Inventors: Steffen Goletz, Berlin (DE); Antje Danielczyk, Panketal (DE); Renate Stahn, Berlin (DE); Uwe Karsten, Panketal (DE)

(73) Assignee: GLYCOTOPE GMBH, Berlin (DE)

(*) Notice: Subject to any disclaimer, the term of this patent is extended or adjusted under 35 U.S.C. 154(b) by 790 days.

(21) Appl. No.: 13/387,587

(22) PCT Filed: Jul. 30, 2010

(86) PCT No.: PCT/EP2010/004663
§ 371 (c)(1),
(2), (4) Date: Jan. 27, 2012

(87) PCT Pub. No.: WO2011/012309
PCT Pub. Date: Feb. 3, 2011

(65) Prior Publication Data
US 2012/0128676 A1 May 24, 2012

Related U.S. Application Data

(60) Provisional application No. 61/230,211, filed on Jul. 31, 2009.

(30) Foreign Application Priority Data

Jul. 31, 2009 (EP) ..................... 09009942

(51) Int. Cl.
*A61K 39/395* (2006.01)
*C07K 16/30* (2006.01)
(52) U.S. Cl.
CPC ......... *C07K 16/3092* (2013.01); *C07K 2317/24* (2013.01); *C07K 2317/56* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,506,343 | A | 4/1996 | Kufe |
| 5,683,674 | A | 11/1997 | Taylor-Papadimitriou et al. |
| 5,739,277 | A | 4/1998 | Presta et al. |
| 5,804,187 | A | 9/1998 | do Couto et al. |
| 6,315,997 | B1 | 11/2001 | do Couto et al. |
| 6,465,220 | B1 | 10/2002 | Hassan et al. |
| 8,779,102 | B2 | 7/2014 | Goletz et al. |
| 2002/0132771 | A1 | 9/2002 | Madiyalakan |
| 2006/0292643 | A1* | 12/2006 | Goletz et al. ............ 435/7.23 |
| 2010/0028947 | A1 | 2/2010 | Goletz et al. |
| 2015/0005474 | A1 | 1/2015 | Goletz et al. |

FOREIGN PATENT DOCUMENTS

| | | |
|---|---|---|
| WO | 93/20841 A1 | 10/1993 |
| WO | 01/12217 A1 | 2/2001 |
| WO | 02/44217 A2 | 6/2002 |
| WO | 2004/009632 A2 | 1/2004 |
| WO | 2004/018659 A1 | 3/2004 |
| WO | 2004/065423 A2 | 8/2004 |
| WO | 2005/017130 A2 | 2/2005 |
| WO | 2005/080585 A1 | 9/2005 |
| WO | 2008/028686 A2 | 3/2008 |
| WO | 2011/012309 A1 | 2/2011 |

OTHER PUBLICATIONS

Rudikoff et al. (Proc Natl Acad Sci USA 1982 vol. 79 p. 1979.*
MacCallum et al. J. Mol. Biol. (1996) 262, 732-745.*
Pascalis et al. (The Journal of Immunology (2002) 169, 3076-3084.*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162.*
Padlan et al. (PNAS 1989, 86:5938-5942.*
Lamminmaki et al. (JBC 2001, 276:36687-36694).*
White et al. (2001, Ann. Rev. Med., 2001, 52:125-145).*
Meibohm (Pharmacokinetics and Pharmacodynamics of Biotech Drugs, Wiley-VHC, 2006, chapter 3, p. 45-91).*
Hinoda, Yuji et al., "Circulating tumor-associated antigens detected by monoclonal antibodies against the polypeptide core of mucin—Comparison of antigen MUSE11 with CA15-3," Gastroenterologia Japonica, vol. 27(3):390-395 (1992).
Holm, Patrik et al., "Functional mapping and single chain construction of the anti-cytokeratin 8 monoclonal antibody TS1," Molecular Immunology, vol. 44:1075-1084 (2007).
Hosse, Ralf J. et al., "A new generation of protein display scaffolds for molecular recognition," Protein Science, vol. 15:14-27 (2006).
Hsieh, Linda C. et al., "Controlling Chemical Reactivity wtih Antibodies," Science, vol. 260:337-339 (1993).
Hufton, Simon E. et al., "Development and application of cytotoxic T lymphocyte-associated antigen 4 as a protein scaffold for the generation of novel binding ligands," FEBS Letters, vol. 475:225-231 (2000).
Hwang, William Ying Khee et al., "Immunogenicity of engineered antibodies," Methods, vol. 36:3-10 (2005).
Hufton, Simon E. et al., "Development and application of cytotoxic T lymphocyte-associated antigen 4 as a protein scaffold for the generation of novel binding ligands," FEBS Letters, vol. 475:225-231 (2000).
Hwang, William Ying Khee et al., "Immunogenicity of engineered antibodies," Methods, vol. 36:3-10 (2005).

(Continued)

*Primary Examiner* — Laura B Goddard
*Assistant Examiner* — Meera Natarajan
(74) *Attorney, Agent, or Firm* — Nelson Mullins Riley & Scarborough LLP; Jane E. Remillard, Esq.; Jill Gorny Sloper, Esq.

(57) ABSTRACT

The present invention pertains to anti-mucin antibodies having improved antigen binding and/or recognition properties as well as a method for improving the antigen binding and/or recognition of an anti-mucin antibody. In particular, the present invention is directed to anti-MUC1 antibodies which are useful in the treatment of cancer.

18 Claims, 4 Drawing Sheets

(56) References Cited

OTHER PUBLICATIONS

Figure 1:
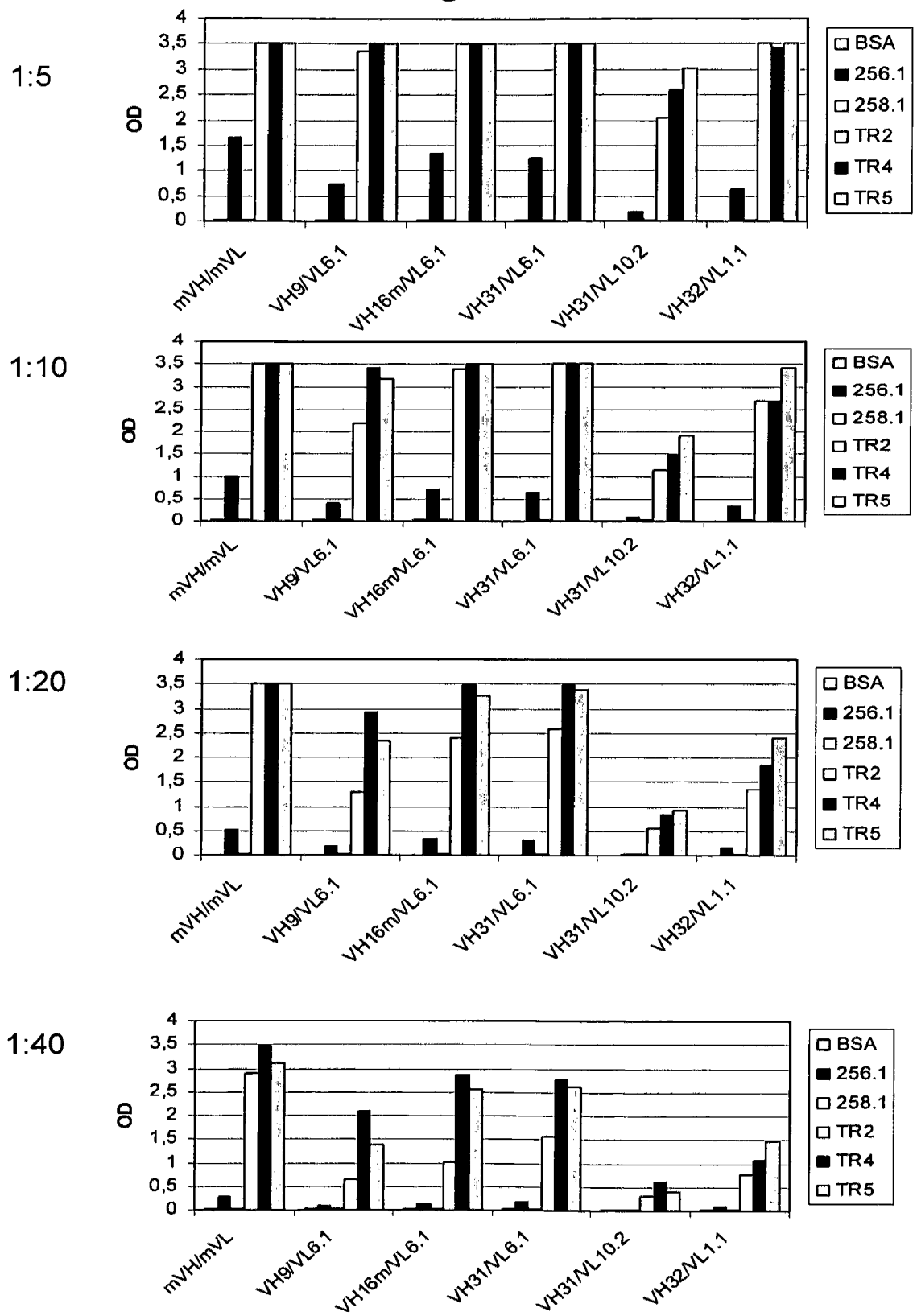

Hwang, William Ying Khee et al., "Use of human germline genes in a CDR homology-based approach to antibody humanization," Methods, vol. 36:35-42 (2005).
Iwahashi, Makoto et al., "CDR substitutions of a humanized monoclonal antibody (CC49): contributions of individual CDRs to antigen binding and immunogenicity," Molecular Immunology, vol. 36:1079-1091 (1999).
Jensen, Kim Bak et al., "Functional improvement of antibody fragments using a novel phage coat protein III fusion system," Biochemical and Biophysical Research Communications, vol. 298:566-573 (2002).
Jeschke, U. et al., "Expression of the Thomsen-Friedenreich antigen and of its putative carrier protein mucin 1 in the human placenta and in trophoblast cells in vitro," Histochem. Cell Biol., vol. 117:219-226 (2002).
Jeschke, Udo et al., "The Human Endometrium Expresses the Glycoprotein Mucin-1 and Shows Positive Correlation for Thomsen-Friedenreich Epitope Expression and Galectin-1 Binding," Journal of Histochemistry & Cytochemistry, vol. 57(9):871-881 (2009).
Johnson, George et al., "Kabat Database and its applications: 30 years after the first variability plot," Nucleic Acids Research, vol. 28(1):214-218 (2000).
Karsten, Uwe et al., "A New Monoclonal Antibody (A78-G/A7) to the Thomsen-Friedenreich Pan-Tumor Antigen," Hybridoma, vol. 14(1):37-43 (1995).
Karsten, Uwe et al., "Binding patterns of DTR-specific antibodies reveal a glycosylation-conditioned tumor-specific epitope of the epithelial mucin (MUC1)," Glycobiology, vol. 14(8):681-692 (2004).
Karsten, Uwe et al., "Enhanced Binding of Antibodies to the Dtr Motif of MUC1 Tandem Repeat Peptide Is Mediated by Site-specific Glycosylation," Cancer Research, vol. 2541-2549 (1998).
Karsten, Uwe et al., "What Makes MUC1 a Tumor Antigen?" Tumor Biology, vol. 26:217-220 (2005).
Kashmiri, S.V.S. et al., "Development of a minimally immunogenic variant of humanized anti-carcinoma monoclonal antibody CC49," Critical Reviews in Oncology/Hematology, vol. 38:3-16 (2001).
Kashmiri, Syed V.S. et al., "SDR grafting—a new approach to antibody humanization," Methods, vol. 36:25-34 (2005).
Kettleborough, Catherine A. et al., "Humanization of a mouse monoclonal antibody by CDR-grafting: the importance of framework residues on loop conformation," Protein Engineering, vol. 4(7):773-783 (1991).
Kostelny, Sheri A. et al., "Humanization and Characterization of the Anti-HLA-DR Antibody 1D10," Int. J. Cancer, vol. 93:556-565 (2001).
Kozak, Robert W. et al., "Nature of the Bifunctional Chelating Agent Used for Radioimmunotherapy with Yttrium-90 Monoclonal Antibodies: Critical Factors in Determining in Vivo Survival and Organ Toxicity," Cancer Research, vol. 49:2639-2644 (1989).
Kuemmel, Andreas et al., "TA-MUC1 epitope in non-small cell lung cancer," Lung Cancer, vol. 63:98-105 (2009).
Kunz, Horst et al., "Synthetic Glycopeptides for the Development of Tumour-Selective Vaccines," J. Peptide Sci., vol. 9:563-573 (2003).
Lazar, Eliane et al.' "Transforming Growth Factor alpha: Mutation of Aspartic Acid 47 and Leucine 48 Results in Different Biological Activities," Molecular and Cellular Biology, vol. 8(3):1247-1252 (1988).
Leung, Shui-On et al., "Construction and Characterization of a Humanized, Internalizing, B-Cell (CD22)-Specific, Leukemia/Lymphoma Antibody, LL2," Molecular Immunology, vol. 32(17118):1413-1427 (1995).
Li, Jia et al., "Where Do We Place PankoMab in the Reagents Used to Study the MUC1 Superfamily/" Onkologie, vol. 32:235-237 (2009).
Liao, Kuang-Wen et al., "Design of Transgenes for Efficient Expression of Active Chimeric Proteins on Mammalian Cells," Biotechnol. Bioeng., vol. 73(4):313-323 (2001).
Libyh, M. Tonye et al., "A Recombinant Human scFv Anti-RH(D) Antibody With Multiple Valences Using a C-Terminal Fragment of C4-Binding Protein," Blood, vol. 90(10):3978-3983 (1997).
Linardou, H. et al., "Deoxyribonuclease I (DNase I), A Novel Approach for Targeted Cancer Therapy," Cell Biophysics, vol. 24-25:243-248 (1994).
Luo, Guang X. et al., "Humanization of an anti-ICAM-1 antibody with over 50-fold affinity and functional improvement," Journal of Immunological Methods, vol. 275:31-40 (2003).
MacCallum, Robert M. et al., "Antibody-antigen Interactions: Contact Analysis and Binding Site Topography," J. Mol. Biol., vol. 262:732-745 (1996).
Martin, Andrew C.R. et al., "Structural Families in Loops of Homologous Proteins: Automatic Classification, Modelling and Application to Antibodies," J. Mol. Biol., vol. 263:800-815 (1996).
Matzinger, Polly et al., "Tolerance, Danger, and the Extended Family," Annu. Rev. Immunol., vol. 12:991-1045 (1994).
Morea, Veronica et al., "Antibody Modeling: Implications for Engineering and Design," Methods, vol. 20:267-279 (2000).
Morrisons, Sherie L. et al., "Complement activation and Fc receptor binding by IgG," Protein Engineering of Antibody Molecules for Prophylactic and Therapeutic Applications in Man, Mike Clark (Ed.), pp. 101-113 (1993).
MSNBC News Services, "Mixed results on new cancer drug, Preliminary studies show endostatin is safe, may help some patients," 4 pages (2000).
Mylonas, Ioannis et al., "Mucin 1, Thomsen-Friedenreich Expression and Galectin-1 Binding in Endometrioid Adenocarcinoma: An Immunohistochemical Analysis," Anticancer Research, vol. 27:1975-1980 (2007).
Nagahira, Kazuhiro et al., "Humanization of a mouse neutralizing monoclonal antibody against tumor necrosis factor-alpha (TNF-alpha)," Journal of Immunological Methods, vol. 222:83-92 (1999).
Nicaise, Magali et al., "Affinity transfer for CDR grafting on a nonimmunoglobulin scaffold," Protein Science, vol. 13:1882-1891 (2004).
Nuttall, Stewart D. et al., "Design and Expression of Soluble CTLA-4 Variable Domain as a Scaffold for the Display of Functional Polypeptides," Proteins: Structure, Function, and Genetics, vol. 36:217-227 (1999).
Nygren, Per-Ake et al., "Scaffolds for engineering novel binding sites in proteins," Current Biology in Structural Biology, vol. 7:463-469 (1997).
Panka, David J. et al., "Variable region framework differences result in decreased or increased affinity of variant anti-digoxin antibodies," Proc. Natl. Acad. Sci. USA, vol. 85:3080-3084 (1988).
Peach, Robert J. et al., "Complementarity Determining Region 1 (CDR1)- and CDR3-analogous Regions in CTLA-4 and CD28 Determine the Binding to B7-1," J. Exp. Med., vol. 180:2049-2058 (1994).
Price, M.R. et al., "Summary report on the ISOBM TD-4 Workshop: analysis of 56 monoclonal antibodies against the MUC1 mucin," Tumour Biol., vol. 19(Suppl. 1):1-20 (1998).
Queen, Cary et al., "A humanized antibody that binds to the interleukin 2 receptor," Proc. Natl. Acad. Sci. USA, vol. 86:10029-10033 (1989).
Richter, D.U. et al., "Expression of the Thomsen-Friedenreich (TF) Antigen in the Human Placenta," Anticancer Research, vol. 20:5129-5134 (2000).
Riechmann, Lutz et al., "Reshaping human antibodies for therapy," Nature, vol. 332:323-327 (1988).
Roguska, Michael A. et al., "Humanization of murine monoclonal antibodies through variable domain resurfacing," Proc. Natl. Acad. Sci. USA, vol. 91:969-973 (1994).
Roguska, Michael A. et al., "A comparison of two murine monoclonal antibodies humanized by CDR-grafting and variable domain resurfacing," Protein Engineering, vol. 9(10):895-904 (1996).
Rooman, Marianne J. et al., "Amino acid sequence templates derived from recurrent turn motifs in proteins: critical evaluation of their predictive power," Protein Engineering, vol. 3(1):23-27 (1989).
U.S. Appl. No. 10/540,479, Steffen Goletz, filed May 10, 2006, Mar. 3, 2014.

(56) References Cited

OTHER PUBLICATIONS

Rosok, Mae Joanne et al., "A Combinatorial Library Strategy for the Rapid Humanization of Anticarcinoma BR96 Fab," The Journal of Biological Chemistry, vol. 271(37):22611-22618 (1996).
Rudikoff, Stuart et al., "Single amino acid substitution altering antigen-binding specificity," Proc. Natl Acad. Sci. USA, vol. 79:1979-1983 (1982).
Saerens, Dirk et al., "Identification of a Universal VHH Framework to Graft Non-canonical Antigen-binding Loops of Camel Single-domain Antibodies," J. Mol. Biol., vol. 352:597-607 (2005).
Saldanha, Jose W. et al., "A single backmutation in the human kIV framework of a previously unsuccessfully humanized antibody restores the binding activity and increases the secretion in cos cells," Molecular Immunology, vol. 36:709-719 (1999).
Singer, Irwin I. et al., "Optimal Humanization of 1B4, an Anti-CD18 Murine Monoclonal Antibody, Is Achieved by Correct Choice of Human V-Region Framework Sequences," The Journal of Immunology, vol. 150(7):2844-2857 (1993).
Sandhu, Jasbir Singh, "A rapid procedure for the humanization of monoclonal antibodies," Gene, vol. 150:409-410 (1994).
Sato, Koh et al., "Reshaping a Human Antibody to Inhibit the Interleukin 6-dependent Tumor Cell Growth," Cancer Research, vol. 53:851-856 (1993).
Sato, Koh et al., "Humanization of a Mouse Anti-Human Interleukin-6 Receptor Antibody Comparing Two Methods for Selecting Human Framework Regions," Molecular Immunology, vol. 31(5):371-381 (1994).
Scheibel, Thomas et al., "Contribution of N- and C-terminal domains to the function of Hsp90 in *Saccharomyces cerevisiae*," Molecular Microbiology, vol. 34(4):701-713 (1999).
Schlapschy, Martin et al., "Functional humanization of an anti-CD30 Fab fragment for the immunotherpy of Hodgkin's lymphoma using an in vitro evolution approach," Protein Engineering, Design & Selection, vol. 17 (12):847-860 (2004).
Schlom, Jeffrey, "Monoclonal Antibodies: They're More and Less Than You Think," Molecular Foundation of Oncology, Samuel Broder (Ed.), William & Wilkins, Baltimore, Chapter 6, pp. 95-134 (1991).
Schneider, Dirk et al., "Thermostability of membrane protein helix-helix interaction elucidated by statistical analysis," FEBS Letters, vol. 532:231-236 (2002).
Schneider, Frank et al., "Overexpression of Sialyltransferase CMP-Sialic Acid: Galbeta1,3GALNAc-R alpha6-Sialyltransferase is Related to Poor Patient Survival in Human Colorectal Carcinomas," Cancer Research, vol. 61:4605-4611 (2001).
Skerra, Arne, "Engineered protein scaffolds for molecular recognition," Journal of Molecular Recognition, vol. 13:167-187 (2000).
Skerra, Arne, "Alternative non-antibody scaffolds for molecular recognition," Current Opinion in Biotechnology, vol. 18:295-304 (2007).
Stimmel, Julie B. et al., "Yttrium-90 Chelation Properties of Tetraazatetraacetic Acid Macrocycles, Diethylenetriaminepentaacetic Acid Analogues, and a Novel Terpyridine Acyclic Chelator," Bioconjugate Chem., vol. 6:219-225 (1995).
Tsurushita, Naoya et al., "Design of humanized antibodies: From anti-Tac to Zenapax," Methods, vol. 36:69-83 (2005).
Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320:415-428 (2002).
Wang, Zhuozhi et al., "Humanization of a mouse monoclonal antibody neutralizing TNF-alpha by guided selection," Journal of Immunological Methods, vol. 241:171-184 (2000).
Wu, Shan et al., "Conformation of Complementarity Determining Region L1 Loop in Murine IgG lambda Light Chain Extends the Repertoire of Canonical Forms," J. Mol. Biol., vol. 229:597-601 (1993).
Wu, Herren et al., "Humanization of a Murine Monoclonal Antibody by Simultaneous Optimization of Framework and CDR Residues," J. Mol. Biol., vol. 294:151-162 (1999).
Yang, Xiao-Dong et al., "Development of ABX-EGF, a fully human anti-EGF receptor monoclonal antibody, for cancer therapy," Critical Reviews in Oncology/Hermatology, vol. 38:17-23 (2001).
International Preliminary Report on Patentability for Application No. PCT/EP2010/004663, dated Jan. 31, 2012.
International Search Report for Application No. PCT/EP2010/004663, dated Dec. 17, 2010.
International Search Report for Application No. PCT/DE2004/000132, 3 pages, dated Sep. 23, 2004.
International Search Report for Application No. PCT/EP2007/007877, 4 pages, dated Apr. 18, 2008.
Adams, Camellia W. et al., "Humanization of a recombinant monoclonal antibody to produce a therapeutic HER dimerization inhibitor, pertuzumab," Cancer Immunol. Immunother., vol. 55:717-727 (2006).
Almagro, Juan C. et al., "Humanization of antibodies," Frontiers in Bioscience, vol. 13:1619-1633 (2008).
Baca, Manuel et al., "Antibody Humanization Using Monovalent Phage Display," The Journal of Biological Chemistry, vol. 272(16):10678-10684 (1997).
Bagshawe, Kenneth D. et al., "Antibody-directed enzyme prodrug therapy (ADEPT) for cancer," Expert Opin. Biol. Ther., vol. 4(11):1777-1789 (2004).
Baldus, Stephan E. et al., "Coexpression of MUC1 Mucin Peptide Core and the Thomsen-Friedenreich Antigen in Colorectal Neoplasms," Cancer, vol. 82:1019-1027 (1998).
Baumeister, Hans et al., "A novel human expression system for production of higher active biotherapeutics with optimised glycosylation," Biopharmaceuticals, pp. 21-24 (2006).
Baumeister, Hans et al., "GlycoEngineering—a Technology for Production of Glycoproteins," BioTOPics24, retrieved online at: http://www.glycotope.com/wp-content/uploads/documents/biotopics241.pdf, 2 pages, (2004).
Baumeister, Hans et al., "GlycoExpress: A novel expression for the optimal glycosylation of biotherapeutics," Speciality Chemicals Magazine, pp. 46-48 (2005).
Boel, Edwin et al., "Functional human monoclonal antibodies of all isotypes constructed from phage display library-derived single-chain Fv antibody fragments," Journal of Immunological Methods, vol. 239:153-166 (2000).
Bohm, C.M. et al., "Carbohydrate Recognition on MUC1-Expressing Targets Enhances Cytotoxicity of a T Cell Subpopulation," Scand. J. Immunol., vol. 46:27-34 (1997).
Brechbiel, Martin W. et al., "Synthesis of 1-(p-Isothiocyanatobenzyl) Derivatives of DTPA and EDTA. Antibody Labeling and Tumor-Imaging Studies," Inorg. Chem., vol. 25:2772-2781 (1986).
Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111:2129-2138 (1990).
Cao, Yi et al., "Immunohistochemical Characterization of a Panel of 56 Antibodies with Normal Human Small Intestine, Colon, and Breast Tissues," Tumor Biol., vol. 19(Suppl. 1):88-99 (1998).
Cao, Yi et al., "Expression of MUC1, Thomsen-Friedenreich antigen, Tn, sialosyl-Tn, and alpha2,6-linked sialic acid in hepatocellular carcinomas and preneoplastic hepatocellular lesions," Virchows Arch, vol. 434:503-509 (1999).
Cao, Yi et al., "Expression of MUC1, Thomsen-Friedenreich-related antigens, and cytokeratin 19 in human renal cell carcinomas and tubular clear cell lesions," Virchows Arch, vol. 436:119-126 (2000).
Cao, Yi et al., "Mucins (MUC1 and MUC3) of Gastrointestinal and Breast Epithelia Reveal Different and Heterogeneous Tumor-associated Aberrations in Glycosylation," The Journal of Histochemistry & Cytochemistry, vol. 45(11):1547-1557 (1997).
Cao, Yi et al., "Binding patterns of 51 monoclonal antibodies to peptide and carbohydrate epitopes of the epithelial mucin (MUC1) on tissue sections of adenolymphomas of the parotid (Warthin's tumours): role of epitope masking by glycans," Histochem Cell Biol, vol. 115:349-356 (2001).
Cao, Yi et al., "Immunodetection of epithelial mucin (MUC1, MUC3) and mucin-associated glycotopes (TF, Tn, and sialosyl-Tn)

(56) References Cited

OTHER PUBLICATIONS in benign and malignant lesions of colonic epithelium: apolar localization corresponds to malignant transformation," Virchows Arch, vol. 431:159-166 (1997).
Casset, Florence et al., "A peptide mimetic of an anti-CD4 monoclonal antibody by rational design," Biochemical and Biophysical Research Communications, vol. 307:198-205 (2003).
Chen, Yvonne et al., "Selection and Anlaysis of an Optimized Anti-VEGF Antibody: Crystal Structure of an Affinity-matured Fab in Complex with Antigen," J. Mol. Biol., vol. 293:865-881 (1999).
Chothia, Cyrus et al., "Canonical Structures for the Hypervariable Regions of Immunoglobulins," J. Mol. Biol., vol. 196:901-917 (1987).
Chothia, Cyrus et al., "Conformations of immunoglobulin hypervariable regions," Nature, vol. 342:877-883 (1989).
Chothia, Cyrus et al., "Structural Repertoire of the Human VH Segments," J. Mol. Biol., vol. 227:799-817 (1992).
Chothia, Cyrus et al., "The Predicted Structure of Immunoglobulin D1.3 and Its Comparison with the Crystal Structure," Science, vol. 233(4765):755-758 (1986).
Clark, Mike, "Antibody humanization: a case of the 'Emperor's new clothes'?" Immunology Today, vol. 21(8):397-402 (2000).
Co, Man Sung et al., "Humanized antibodies for therapy," Nature, vol. 351:501-502 (1991).
Couto, Joseph R. et al., "Designing Human Consensus Antibodies with Minimal Positional Templates," Cancer Research, vol. 55:(Suppl.):5573s-5977s (1995).
Dai, Jian et al., "Effect of Desialylation on Binding, Affinity, and Specificity of 56 Monoclonal Antibodies against MUC1 Mucin," Tumor Biol, vol. 19(Suppl. 1):100-110 (1998).
Dall'Acqua, William F. et al., "Antibody humanization by framework shuffling," Methods, vol. 36:43-60 (2005).
Danielczyk, Antje et al., "PankoMab: a potent new generation anti-tumour MUC1 antibody," Cancer Immunol. Immunother., vol. 55(11):1337-1347 (2006).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169:3076-3084 (2002).
Dermer, Gerald B., "Another Anniversary for the War on Cancer," Bio/Technology, vol. 12:320 (1994).
Dian, Darius et al., "Evaluation of a Novel Anti-Mucin 1 (MUC1) Antibody (PankoMab) as a Potential Diagnostic Tool in Human Ductal Breast Cancer: Comparison with Two Established Antibodies," Onkologie, vol. 32:238-244 (2009).
Duk, Maria et al., "Purification of Human Anti-TF (Thomsen-Friedenreich) and Anti-Tn Antibodies by Affinity Chromatography on Glycophorin A Derivatives and Characterization of the Antibodies by Microtiter Plate ELISA," Archivum Immunologiae et Therapiae Experimentalis, vol. 46:69-77 (1998).
European Patent Application 07 818 090.8, Annex 1, 4 pages, dated Jan. 14, 2011.
European Patent Application 07 818 090.8, Annex 2, 4 pages, dated Jan. 14, 2011.
European Patent Application 07 818 090.8, Annex 2, 7 pages, dated Feb. 6, 2012.
Euhus, David M. et al., "Appraisal of Anti-idiotypic Antibodies in the Treatment of Solid Tumors in Humans," Surg. Glnecol. Obstet., vol. 175(1):89-96 (1992).
Fan, Xiao-Na et al., "Reactivity of a humanized antibody (hPankoMab) towards a tumor-related MUC1 epitope (TA-MUC1) with various human carcinomas," Pathol. Res. Pract., vol. 206(8):585-589 (2010).
Fiebig, H.H. et al., "Clonogenic assay with established human tumour xenografts: correlation of in vitro to in vivo activity as a basis for anticancer drug discovery," European Journal of Cancer, vol. 40:802-820 (2004).
Freshney, R. Ian, "Culture of Animal Cells, A Manual of Basic Technique," Alan R. Liss, Inc., New York, p. 4 (1983).
Glycotope, "Turning Glycomics into Health," Biotech Business Opportunities in Germany, Bio 2006 Annual Convention in Chicago, 12 pages, (2006).
Goletz, S. et al., "Binidng Patterns of 33 TD-4 (MUC1) Antibodies Towards Single-Chain Fragments and Peptides Mimicking the Conformation of the MUC1 PDTRP Epitope," Tumor Biology, vol. 21(Suppl. 1):142 (2000).
Goletz, Steffen et al., "Structure Analysis of Acetylated and Non-acetylated O-Linked MUC1-Glycopeptides by Post-source Decay Matrix-assisted Laser Desorption/Ionization Mass Spectrometry," Rapid Communications in Mass Spectrometry, vol. 11:1387-1398 (1997).
Goletz, Steffen et al., "Selection of Large Diversities of Antiidiotypic Antibody Fragments by Phage Display," J. Mol. Biol., vol. 315:1087-1097 (2002).
Gollasch, H. et al., "Identification of Immunogenic Peptide-Mimics for the Thomsen-Friedenreich-Glycoantigen," Ann. Hematol., vol. 77(Suppl.):s84 (1998).
Gonzales, Noreen R. et al., "Minimizing the Immunogenicity of Antibodies for Clinical Application," Tumor Biol., vol. 26:31-43 (2005).
Green, Douglas R. et al., "Activation-induced cell death in T cells," Immunological Reviews, vol. 193:70-81 (2003).
Grunberg, Elke et al., "Effects of Differentiation Inducers on Cell Phenotypes of Cultured Nontransformed and Immortalized Mammary Epithelial Cells: A Comparative Immunocytochemical Analysis," Tumor Biol., vol. 21:211-223 (2000).
Herrera, Antonieta M. et al., "Efficiency of Erythropoietin's Signal Peptide for HIVMN-1 gp 120 Expression," Biochemical and Biophysical Research Communications, vol. 273:557-559 (2000).
U.S. Appl. No. 14/316,389, filed Jun. 26, 2014, Steffen Goletz.
U.S. Appl. No. 10/540,479, Steffen Goletz, filed May 10, 2006, Oct. 8, 2013.
U.S. Appl. No. 12/440,562, Steffen Goletz, filed May 14, 2009, Jul. 15, 2014.
Möller, Heiko et al, "NMR-based determination of the binding epitope and conformational analysis of MUC-1 glycopeptides and peptides bound to the breast cancer-selective monoclonal antibody SM3," European Journal of Biochemistry, vol. 269(5):1444-1455 (2002).
Sørensen, Anne Louise et al., "Chemoenzymatically synthesized multimeric Tn/STn MUC1 glycopeptides elicit cancer-specific anti-MUC1 antibody responses and override tolerance," Glycobiology, vol. 16(2): 96-107 (2005).
U.S. Appl. No. 14/703,498, filed May 4, 2015, Steffen Goletz.

* cited by examiner

MUC1 ANTIBODIES

FIELD OF THE INVENTION

The present invention pertains to the field of antibodies. In particular, improved anti-mucin antibodies showing an improved antigen binding and/or recognition as well as a method for improving the antigen binding and/or recognition of an anti-mucin antibody are provided. In specific embodiments, the present invention is directed to improved anti-MUC1 antibodies which are useful in the treatment of cancer.

BACKGROUND OF THE INVENTION

Today, antibodies are widely used agents in the field of medicine and research. In medicine, they find application in many different fields. For example, antibodies are used as labeling agents for detecting certain markers which allow the diagnosis and/or prognosis of diseases or the determination of specific body parameters such as, for example, the presence or concentration of certain hormones.

Furthermore, antibodies are also used as therapeutic agents in the treatment and prophylaxis of a variety of diseases such as cancer, cardiovascular diseases, inflammatory diseases, macular degeneration, transplant rejection, multiple sclerosis, and viral infections. In these therapies, the antibody may possess therapeutic activity on it own, for example by blocking receptors or messenger molecules, thereby inhibiting their disease-relevant functions, or by recruiting and activating components of the patient's immune system. Alternatively, the antibody may be coupled to another agent having therapeutic activity. In particular in the treatment of cancer and infections, said further agent has cell-killing activity and may be, for example a radioisotope or a cytotoxin. In another application, antibodies may be used to passively immunize a patient by transferring suitable antibodies into the patient's circulation.

Specific antibodies are produced by injecting an antigen into a mammal, such as a mouse, rat, rabbit, goat, sheep, or horse. Blood isolated from these animals contains polyclonal antibodies directed against said antigen in the serum. To obtain an antibody that is specific for a single epitope of an antigen, antibody-secreting lymphocytes are isolated from the animal and immortalized by fusing them with a cancer cell line, resulting in hybridoma cells. Single hybridoma cells are then isolated by dilution cloning to generate cell clones that all produce the same monoclonal antibody.

However, in therapeutic applications these monoclonal antibodies have the problem that they are derived from animal organisms and differ in their amino acid sequence from human antibodies. The human immune system hence recognizes these animal antibodies as foreign and rapidly removes them from circulation. Furthermore, systemic inflammatory effects may be caused. A solution to this problem is the replacement of certain constant parts of the monoclonal antibody with corresponding parts of a human antibody. If only the heavy and light chain constant regions are replaced, a chimeric antibody is obtained, while the additional replacement of the framework regions of the heavy and light chain variable regions results in so called humanized antibodies.

In research, purified antibodies are used in many applications. They are most commonly used to identify and locate biological molecules such as in particular proteins. The biological molecules may either be detected after they have been isolated, for example to determine their presence, concentration, integrity or size. On the other hand, they may be detected in cellular or tissue samples, for example to determine their presence or location. Furthermore, antibodies are used in isolation procedures of specific biological substances, in particular proteins, wherein the antibody specifically separates the biological substance of interest from the sample containing it.

In all these applications, a tight binding and specific recognition of the antigen is of vital importance for the antibody used. Thereby, higher activity and less cross-reactivity, in particular less adverse side effects in therapeutic applications, are obtained. However, during humanization of monoclonal antibodies, often the affinity and specificity of the engineered antibody is decreased.

An interesting and important group of antibodies are those directed against mucin proteins. Mucins are a family of high molecular weight, heavily glycosylated proteins produced by many epithelial tissues in vertebrates. They can be subdivided into mucin proteins which are membrane-bound due to the presence of a hydrophobic membrane-spanning domain that favors retention in the plasma membrane, and mucins which are secreted onto mucosal surfaces or secreted to become a component of saliva. The human mucin protein family consists of at least the family members MUC1, MUC2, MUC3A, MUC3B, MUC4, MUC5AC, MUC5B, MUC6, MUC7, MUC8, MUC12, MUC13, MUC15, MUC16, MUC17, MUC19, and MUC20; wherein MUC1, MUC3A (isoform 1), MUC3B and MUC4 are membrane bound.

Increased mucin production occurs in many adenocarcinomas, including cancer of the pancreas, lung, breast, ovary, colon, etc. Mucins are also overexpressed in lung diseases such as asthma, bronchitis, chronic obstructive pulmonary disease or cystic fibrosis. Two membrane mucins, MUC1 and MUC4 have been extensively studied in relation to their pathological implication in the disease process. Moreover, mucins are also being investigated for their potential as diagnostic markers.

Several antibodies directed against mucin proteins, in particular MUC1, are known in the art. Some of them are already approved for medical applications. However, their use could still be improved if their antigen affinity and/or specificity could be enhanced.

In view of this, there is a need in the art to provide improved anti-mucin antibodies preferably having enhanced antigen binding and/or recognition properties as well as methods which are suitable to improve the antigen binding and/or recognition of known antibodies, in particular of therapeutic MUC1 antibodies.

SUMMARY OF THE INVENTION

The present inventors have found that the antigen-binding properties of antibodies directed against mucin proteins are good if a proline residue is present at position 28 of the heavy chain variable region of an antibody, according to the Kabat numbering.

Therefore, in a first aspect, the present invention is directed to an antibody or a fragment or derivative thereof which is capable of binding to a mucin protein and which comprises at least a portion of the heavy chain variable region which comprises a proline residue at amino acid position 28 according to the Kabat numbering.

In a second aspect, the present invention provides a nucleic acid encoding the antibody or fragment or derivative thereof according to the invention. Furthermore, in a third aspect an expression cassette or vector comprising the nucleic acid according to the invention and a promoter operatively connected with said nucleic acid and, in a fourth aspect, a host cell comprising the nucleic acid or the expression cassette or vector according to the invention are provided.

In a fifth aspect, the present invention is directed to a composition comprising the antibody or fragment or derivative thereof according to the invention, the nucleic acid according to the invention, the expression cassette or vector according to the invention, or the host cell according to the invention.

According to a sixth aspect, the invention provides the antibody or fragment or derivative thereof, the nucleic acid, the expression cassette or vector, the host cell, or the composition according to the invention for use in medicine, in particular in the treatment, prognosis, diagnosis and/or monitoring of cancer, wherein the cancer preferably is selected from the group consisting of cancer of the colon, stomach, liver, pancreas, kidney, blood, lung, and ovary.

In a seventh aspect, the invention is directed to a method for improving the antigen binding and/or recognition of an antibody or a fragment or derivative thereof which is capable of binding to a mucin protein and which comprises a heavy chain variable region, comprising the step of providing a proline residue at position 28 of the heavy chain variable region, according to the Kabat numbering.

In an eighth aspect, the invention is directed to a method for preparing a nucleic acid according to the invention, comprising the steps of
  (a) providing a nucleic acid comprising the nucleic acid sequence coding for an antibody or a fragment or derivative thereof which is capable of binding to MUC1 and which comprises a heavy chain variable region, wherein the heavy chain variable region does not comprise a proline residue at amino acid position 28 according to the Kabat numbering;
  (b) introducing a mutation into the codon coding for amino acid number 28, according to the Kabat numbering, of the heavy chain variable region so that said codon codes for a proline residue.

Other objects, features, advantages and aspects of the present invention will become apparent to those skilled in the art from the following description and appended claims. It should be understood, however, that the following description, appended claims, and specific examples, which indicate preferred embodiments of the application, are given by way of illustration only. Various changes and modifications within the spirit and scope of the disclosed invention will become readily apparent to those skilled in the art from reading the following.

DETAILED DESCRIPTION OF THE INVENTION

Definitions

As used herein, the following expressions are generally intended to preferably have the meanings as set forth below, except to the extent that the context in which they are used indicates otherwise.

The expression "comprise", as used herein, besides its literal meaning also includes and specifically refers to the expressions "consist essentially of" and "consist of". Thus, the expression "comprise" refers to embodiments wherein the subject-matter which "comprises" specifically listed elements does not comprise further elements as well as embodiments wherein the subject-matter which "comprises" specifically listed elements may and/or indeed does encompass further elements. Likewise, the expression "have" is to be understood as the expression "comprise", also including and specifically referring to the expressions "consist essentially of" and "consist of".

The term "antibody" particularly refers to a protein comprising at least two heavy chains and two light chains connected by disulfide bonds. The term "antibody" includes naturally occurring antibodies as well as all recombinant forms of antibodies, e.g., antibodies expressed in prokaryotes, unglycosylated antibodies, humanized antibody, and chimeric antibody. Each heavy chain is comprised of a heavy chain variable region (VH) and a heavy chain constant region (CH). Each light chain is comprised of a light chain variable region (VL) and a light chain constant region (CL). The heavy chain-constant region comprises three or—in the case of antibodies of the IgM- or IgE-type—four heavy chain-constant domains (CH1, CH2, CH3 and CH4) wherein the first constant domain CH1 is adjacent to the variable region and may be connected to the second constant domain CH2 by a hinge region. The light chain-constant region consists only of one constant domain. The variable regions can be further subdivided into regions of hypervariability, termed complementarity determining regions (CDRs), interspersed with regions that are more conserved, termed framework regions (FR), wherein each variable region comprises three CDRs and four FRs. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. The term "antibody" according to the invention, however, also includes unusual antibodies such as heavy chain antibodies, i.e. antibodies only composed of one or more, in particular two heavy chains, and nanobodies, i.e. antibodies only composed of a single monomeric variable domain.

For indicating the amino acid positions of the heavy chain and light chain variable regions, the Kabat numbering system is used herein (Kabat, E. A. et al. (1991) *Sequences of Proteins of Immunological Interest*, 5$^{th}$ edition, NIH Publication No. 91-3242). According to said system, the heavy chain comprises amino acid positions from position 0 to position 113 including position 35A, 35B, 52A to 52C, 82A to 82C and 100A to 100K. The CDRs of the heavy chain variable region are located, according to the Kabat numbering, at positions 31 to 35B (CDR1), 50 to 65 (CDR2) and 95 to 102 (CDR3). The remaining amino acid positions form the framework regions FR1 to FR4. The light chain variable region comprises positions 0 to 109 including positions 27A to 27F, 95A to 95F and 106A. The CDRs are located at positions 24 to 34 (CDR1), 50 to 56 (CDR2) and 89 to 97 (CDR3). Depending on the initial formation of the specific gene of an antibody, not all of these positions have to be present in a given heavy chain variable region or light chain variable region. In case an amino acid position in a heavy chain or light chain variable region is mentioned herein, unless otherwise indicated it is referred to the position according to the Kabat numbering.

A "fragment or derivative" of an antibody in particular is a protein or glycoprotein which is derived from said antibody and is capable of binding to the same antigen, in particular to the same epitope as the antibody. Thus, a fragment or derivative of an antibody herein generally refers to a functional fragment or derivative. In particularly preferred embodiments, the fragment or derivative of an antibody comprises a heavy chain variable region. It has been shown that the antigen-binding function of an antibody can be performed by fragments of a full-length antibody or derivatives thereof.

Examples of fragments or derivatives of an antibody include (i) Fab fragments, monovalent fragments consisting of the variable region and the first constant domain of each the heavy and the light chain; (ii) F(ab)$_2$ fragments, bivalent fragments comprising two Fab fragments linked by a disulfide bridge at the hinge region; (iii) Fd fragments consisting of the variable region and the first constant domain CH1 of the heavy chain; (iv) Fv fragments consisting of the heavy chain and light chain variable region of a single arm of an antibody; (v) scFv fragments, Fv fragments consisting of a single polypeptide chain; (vi) (Fv)$_2$ fragments consisting of two Fv fragments covalently linked together; (vii) a heavy chain variable domain; and (viii) multibodies consisting of a heavy chain variable region and a light chain variable region covalently linked together in such a manner that association of the heavy chain and light chain variable regions can only occur intermolecular but not intramolecular. These antibody fragments and derivatives are obtained using conventional techniques known to those with skill in the art.

A target amino acid sequence is "derived" from a reference amino acid sequence, for example, if the target amino acid sequence shares a homology or identity over its entire length with a corresponding part of the reference amino acid sequence of at least 60%, preferably at least 70%, at least 75%, more preferably at least 80%, at least 85%, at least 90%, at least 93%, at least 95% or at least 97%. For example, if a framework region of a humanized antibody is derived from a variable region of a particular human antibody, then the amino acid of the framework region of the humanized antibody shares a homology or identity over its entire length with the corresponding framework region of the human antibody of at least 60%, preferably at least 70%, at least 75%, more preferably at least 80%, at least 85%, at least 90%, at least 93%, at least 95% or at least 97%. The "corresponding part" or "corresponding framework region" means that, for example, framework region 1 of a heavy chain variable region (FRH1) of a target antibody corresponds to framework region 1 of the heavy chain variable region of the reference antibody. The same is true, for example, for FRH2, FRH3, FRH4, FRL1, FRL2, FRL3 and FRL4. In particular embodiments, a target amino acid sequence which is "derived" from a reference amino acid sequence is 100% homologous, or in particular 100% identical, over its entire length with a corresponding part of the reference amino acid sequence.

"Specific binding" preferably means that an agent such as an antibody binds stronger to a target such as an epitope for which it is specific compared to the binding to another target. An agent binds stronger to a first target compared to a second target if it binds to the first target with a dissociation constant ($K_d$) which is lower than the dissociation constant for the second target. Preferably the dissociation constant for the target to which the agent binds specifically is more than 2-fold, preferably more than 5-fold, more preferably more than 10-fold, even more preferably more than 20-fold, 50-fold, 100-fold, 200-fold, 500-fold or 1000-fold lower than the dissociation constant for the target to which the agent does not bind specifically.

As used herein, the term "protein" refers to a molecular chain of amino acids or a complex of more than one amino acid chain. A protein can contain any of the naturally occurring amino acids as well as artificial amino acids and can be of biologic or synthetic origin. A protein may be modified, naturally (post-translational modifications) or synthetically, by e.g. glycosylation, amidation, carboxylation and/or phosphorylation. A protein comprises at least two amino acids, but does not have to be of any specific length; this term does not include any size restrictions. In the present application, the terms "protein", "polypeptide" and "peptide" are used interchangeably. Preferably, a protein comprises at least 10 amino acids, preferably at least 50 amino acids, at least 100 amino acids and most preferred at least 100 amino acids.

The term "nucleic acid" includes single-stranded and double-stranded nucleic acids and ribonucleic acids as well as deoxyribonucleic acids. It may comprise naturally occurring as well as synthetic nucleotides and can be naturally or synthetically modified, for example by methylation, 5'- and/or 3'-capping.

The term "conjugate" particularly means two or more compounds which are linked together so that at least some of the properties from each compound are retained in the conjugate. Linking may be achieved by a covalent or non-covalent bond. Preferably, the compounds of the conjugate are linked via a covalent bond. The different compounds of a conjugate may be directly bound to each other via one or more covalent bonds between atoms of the compounds. Alternatively, the compounds may be bound to each other via a linker molecule wherein the linker is covalently attached to atoms of the compounds. If the conjugate is composed of more than two compounds, then these compounds may, for example, be linked in a chain conformation, one compound attached to the next compound, or several compounds each may be attached to one central compound.

The term "expression cassette" in particular refers to a nucleic acid construct which is capable of enabling and regulating the expression of a coding nucleic acid sequence introduced therein. An expression cassette may comprise promoters, ribosome binding sites, enhancers and other control elements which regulate transcription of a gene or translation of an mRNA. The exact structure of expression cassette may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the operatively connected nucleic acid. Expression cassettes may also comprise enhancer sequences or upstream activator sequences.

According to the invention, the term "promoter" refers to a nucleic acid sequence which is located upstream (5') of the nucleic acid sequence which is to be expressed and controls expression of the sequence by providing a recognition and binding site for RNA-polymerases. The "promoter" may include further recognition and binding sites for further factors which are involved in the regulation of transcription of a gene. A promoter may control the transcription of a prokaryotic or eukaryotic gene. Furthermore, a promoter may be "inducible", i.e. initiate transcription in response to an inducing agent, or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

The term "vector" is used here in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes. The term "plasmid" as used herein generally relates to a construct of extrachromosomal genetic material, usually a circular DNA duplex, which can replicate independently of chromosomal DNA.

According to the invention, the term "host cell" relates to any cell which can be transformed or transfected with an exogenous nucleic acid. The term "host cells" comprises according to the invention prokaryotic (e.g. *E. coli*) or eukaryotic cells (e.g. mammalian cells, in particular human cells, yeast cells and insect cells). Particular preference is given to mammalian cells such as cells from humans, mice, hamsters, pigs, goats, or primates. The cells may be derived from a multiplicity of tissue types and comprise primary cells and cell lines. A nucleic acid may be present in the host cell in the form of a single copy or of two or more copies and, in one embodiment, is expressed in the host cell.

The term "patient" means according to the invention a human being, a nonhuman primate or another animal, in particular a mammal such as a cow, horse, pig, sheep, goat, dog, cat or a rodent such as a mouse and rat. In a particularly preferred embodiment, the patient is a human being.

The term "cancer" according to the invention in particular comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

By "tumor" is meant a group of cells or tissue that is formed by misregulated cellular proliferation. Tumors may show partial or complete lack of structural organization and functional coordination with the normal tissue, and usually form a distinct mass of tissue, which may be either benign or malignant.

By "metastasis" is meant the spread of cancer cells from its original site to another part of the body. The formation of metastasis is a very complex process and normally involves detachment of cancer cells from a primary tumor, entering the body circulation and settling down to grow within normal tissues elsewhere in the body. When tumor cells metastasize, the new tumor is called a secondary or metastatic tumor, and its cells normally resemble those in the original tumor. This means, for example, that if breast cancer metastasizes to the lungs, the secondary tumor is made up of abnormal breast cells, not of abnormal lung cells. The tumor in the lung is then called metastatic breast cancer, not lung cancer.

The term "pharmaceutical composition" particularly refers to a composition suitable for administering to a human or animal, i.e., a composition containing components which are pharmaceutically acceptable. Preferably, a pharmaceutical composition comprises an active compound or a salt or prodrug thereof together with a carrier, diluent or pharmaceutical excipient such as buffer, preservative and tonicity modifier.

The present invention is based on the finding that anti-mucin antibodies comprising a proline residue at amino acid position 28, according to the Kabat numbering, in the heavy chain variable region (VH) exhibit good antigen binding properties. Amino acid position 28 of the heavy chain variable region is located in the first framework region (FR1) in the vicinity of complementarity determining region 1 (CDR1). Commonly, in human antibodies a threonine or serine residue is located at this position. For example, the 229 human germ line sequences of antibodies listed in the database of the NCBI all comprise a threonine or serine residue at position 28 of the heavy chain variable region. In particular in the humanization of monoclonal antibodies, it is generally taught in the art to use a threonine or serine residue at position 28 of the heavy chain variable region.

Based on the obtained data it appears that a proline at position 28 of the VH beneficially influences the structural properties of the CDR1. In particular, said proline residue apparently enables the CDR1 to adapt a three-dimensional structure which fits best to the structure of the MUC1 antigen. Thereby, the properties of the antibody can be improved.

In view of these findings, the present invention provides, in a first aspect, an antibody or a fragment or derivative thereof which is capable of binding to a mucin protein and which comprises at least a portion of the heavy chain variable region which comprises a proline residue at amino acid position 28 according to the Kabat numbering.

In preferred embodiments, the portion of the heavy chain variable region comprised by the antibody or a fragment or derivative thereof according to the invention has a length of at least 50 amino acids, preferably at least 70 amino acids, at least 90 amino acids, at least 100 amino acids or at least 110 amino acids. More preferably, the portion of the heavy chain variable region at least comprises the entire framework region 1 and at least one, preferably two or all three CDRs. Most preferably, the antibody or a fragment or derivative thereof according to the invention comprises the complete heavy chain variable region which comprises a proline residue at amino acid position 28 according to the Kabat numbering.

The antibody or fragment or derivative thereof according to the invention may be capable of specifically binding one or more of the proteins of the mucin family, such as MUC1, MUC2, MUC3A, MUC3B, MUC4, MUC5AC, MUC5B, MUC6, MUC7, MUC8, MUC12, MUC13, MUC15, MUC16, MUC17, MUC19, and/or MUC20. Preferably, the antibody or fragment or derivative thereof according to the invention is capable of specifically binding one or more of the membrane-bound mucins MUC1, MUC3A (isoform 1), MUC3B and MUC4, most preferably MUC1. In preferred embodiments, it specifically binds to tumor-associated MUC1 but not or to a much lesser extent to MUC1 of normal, non-tumor cells. In particular, the antibody or fragment or derivative thereof according to the invention binds to the extracellular domain of MUC1, preferably the tandem repeats thereof, most preferably in a conformation-dependent and/or glycosylation-dependent manner, especially if said tandem repeats are glycosylated at a threonine residue with N-acetyl galactosamine (Tn), sialyl α2-6 N-acetyl galactosamine (sTn), galactose β1-3 N-acetyl galactosamine (TF) or galactose β1-3 (sialyl α2-6) N-acetyl galactosamine (sTF), preferably with Tn or TF. Preferably, the carbohydrate moiety is bound to the threonine residue by an α-O-glycosidic bond.

Particular preferred anti-mucin antibodies according to the invention are antibodies which are capable of specifically binding an epitope comprising a peptide moiety. The epitope preferably is a glycosylated peptide moiety and the specific binding of the antibody preferably is dependent on the glycosylation of the epitope, in particular on the specific glycosylation pattern of the epitope. That is, in preferred embodiments the binding affinity of the antibody towards its antigen is higher if the specific epitope bound by the antibody carries a carbohydrate moiety, compared to the epitope not carrying a carbohydrate moiety. In another preferred embodiment, the affinity is higher if the epitope on the mucin protein carries a specific carbohydrate moiety, compared to the epitope carrying another or no carbohydrate moiety. In this case, the affinity towards the antigen wherein the epitope carries another carbohydrate moiety may even be lower than towards an antigen having a non-glycosylated epitope. In these embodiments, the epitope which is bound by the antibody may comprise a peptide part as well as a carbohydrate part. That is, the antibody binds to a peptide moiety and to a carbohydrate moiety.

However, the antibody may alternatively only bind to a peptide moiety. In this embodiment, the carbohydrate moiety attached to the peptide epitope is not bound by the antibody. However, the carbohydrate moiety may nevertheless have an influence on the antibody binding in that it influences the three-dimensional structure of the peptide moiety of the epitope. Here, the flexibility and the three-dimensional structure of the epitope depend on whether, and preferably which, carbohydrate moiety is bound thereto. The antibody then preferably binds to an epitope having a three-dimensional structure which is adopted when a carbohydrate moiety, in particular a specific carbohydrate moiety is bound to the epitope. In the above embodiments, the specific carbohydrate moiety which causes enhanced binding of the antibody when bound to the epitope preferably is N-acetyl galactosamine (Tn), sialyl α2-6 N-acetyl galactosamine (sTn) galactose β1-3 N-acetyl galactosamine (TF) or galactose β1-3 (sialyl α2-6) N-acetyl galactosamine (sTF), preferably Tn or TF. Preferably, the carbohydrate moiety is bound to the peptide moiety by an α-O-glycosidic bond.

Thus, in a further embodiment, the specific binding of the antibody to its epitope is dependent on the conformation of the epitope. As described above, the conformation of the epitope may be dependent on the glycosylation pattern of the epitope. However, the conformation may also depend on the context in which the epitope is presented, for example the overall three-dimensional structure of the protein comprising the epitope. In essence, in case the binding of the antibody to the epitope is conformation dependent, the epitope is capable of adopting different three-dimensional conformations and the binding affinity of the antibody towards one or more of the conformations of the epitope is higher than towards the other conformations of the epitope. In particular, the antibody is only able to bind to the epitope if the epitope exhibits (a) specific conformation(s).

In particularly preferred embodiments, the antibody is capable of specifically binding an epitope comprising the amino acid sequence PDTR (SEQ ID NO: 49) or, more preferably PDTRP (SEQ ID NO: 50). The binding to this epitope preferably is glycosylation dependent, as described above, wherein in particular the binding is increased if a carbohydrate moiety is attached to the threonine residue of the sequence PDTR or PDTRP, respectively. Preferably, the binding is increased if the epitope is glycosylated at the threonine residue with a carbohydrate moiety selected from the group consisting of N-acetyl galactosamine (Tn), sialyl α2-6 N-acetyl galactosamine (sTn), galactose β1-3 N-acetyl galactosamine (TF) and galactose β1-3 (sialyl α2-6) N-acetyl galactosamine (sTF), preferably with Tn or TF. Preferably, the carbohydrate moiety is bound to the threonine residue by an α-O-glycosidic bond. In some embodiments, the glycosylation dependency of the binding is due to the specific conformation the epitope adopts when glycosylated, in particular by the specific carbohydrate moieties mentioned above. In this case, the antibody does not necessarily have to bind to the carbohydrate moiety but may only bind to the peptide moiety of the epitope wherein the affinity of this binding depends on the conformation of the epitope. Preferably, the epitope is comprised in the extracellular tandem repeats of a mucin protein, in particular MUC1. In particular, the antibody according to the invention is capable of binding to a tumor-associated mucin epitope, in particular a tumor-associated MUC1 epitope such as epitope TA-MUC1 (see Karsten, U. et al. (2004) Glycobiology 14, 681-692 and Danielczyk, A. et al. (2006) Cancer Immunol. Immunother. 55, 1337-1347). Preferably, the binding of the antibody according to the invention to cells expressing the tumor-associated MUC1 epitope is stronger than the binding to cells expressing normal, non-tumor MUC1. Preferably, said binding is at least 1.5-fold stronger, preferably at least 2-fold stronger, at least 5-fold stronger, at least 10-fold stronger or at least 100-fold stronger.

A tumor-associated mucin epitope, in particular a MUC1 tumor epitope, preferably refers to an epitope of a mucin protein, in particular MUC1, which is present on tumor cells but not on normal cells and/or which is only accessible by antibodies in the host's circulation when present on tumor cells but not when present on normal cells. In particular, a MUC1 tumor epitope preferably is an epitope comprising at least one PDTRP sequence of the MUC1 tandem repeats and being glycosylated at the threonine of the PDTRP sequence with N-acetyl galactosamine (Tn) or galactose β1-3 N-acetyl galactosamine (TF), preferably via an α-O-glycosidic bond. For tumor specific MUC1 binding, the antibody or fragment or derivative thereof preferably specifically binds the glycosylated MUC1 tumor epitope such that the strength of the bond is increased at least by a factor 2, preferably a factor of 4 or a factor of 10, most preferably a factor of 20 in comparison with the bond to the non-glycosylated peptide of identical length and identical peptide sequence. The binding strength may be measured, for example, using ELISA wherein the target epitope is immobilized and the binding of the antibody or fragment or derivative thereof according to the invention is detected using an enzyme-linked, in particular peroxidase-linked secondary antibody and a suitable detection reagent. An exemplary binding assay is described in WO 2004/065423, e.g. in example 5.1.

Furthermore, the antibody may exhibit antigen binding properties similar to those of the reference antibody PankoMab comprising a heavy chain variable region with the amino acid sequence of SEQ ID NO: 29 and a light chain variable region with the amino acid sequence of SEQ ID NO: 30. In particular, the antibody according to the invention may specifically bind to the same antigen, preferably the same epitope, as the PankoMab, and may preferably bind to said antigen or epitope, respectively, with a comparable affinity. That is, the antibody preferably binds to the antigen or epitope with an affinity having a dissociation constant which is at most 100-fold higher than that of PankoMab, more preferably at most 10-fold higher, and most preferably the dissociation constant is the same as or lower than that of PankoMab. Moreover, the antibody preferably shows cross-specificity with the reference antibody PankoMab. In particular, the antibody is able to block the binding of PankoMab to MUC1 if present in a high enough concentration. This may be possible if the binding of PankoMab to MUC1 is hindered when the antibody according to the invention is already bound to the antigen MUC1.

The inhibition of the binding of PankoMab may be due to, for example, a steric hindrance, i.e. the antibody according to the invention occupies a part of the space which PankoMab would need in order to properly bind to MUC1, or a conformational hindrance, i.e. due to the binding of the antibody according to the invention the epitope of PankoMab adopts a conformation which is unfavorable for the binding of PankoMab.

According to a preferred embodiment the antibody has the following characteristics:
(a) it specifically binds the glycosylated MUC1 tumor epitope, and
(b) it comprises a heavy chain variable region comprising the amino acid sequence of SEQ ID NO: 16 and a light chain variable region comprising the amino acid sequence of SEQ ID NO: 28;

or it is a functional fragment or derivative of the antibody having the characteristics (a) and (b) said functional fragment or derivative showing cross-specificity with an antibody comprising the amino acid sequence of SEQ ID NO: 16 and SEQ ID NO: 28.

The above described embodiments regarding the antibody according to the invention and its antigen and/or epitope binding properties can in the same manner be applied to the fragment or derivative thereof according to the invention.

The antibody according to the invention preferably is a monoclonal antibody. Furthermore, the antibody preferably is a human, murine, goat, primate or camel antibody or is derived therefrom. It may be a chimeric or humanized antibody. It may be an antibody of any isotype or subclass thereof, in particular of the IgG, IgM, IgA, IgE or IgD isotype or a subclass thereof such as IgG1. Preferably, the fragment or derivative of the antibody according to the invention is selected from the group consisting of a Fab fragment, a F(ab)$_2$ fragment, a Fd fragment, a Fv fragment, a scFv fragment, a (Fv)$_2$ fragment, and a multibody. The antibody or fragment or derivative thereof may be a single chain construct comprising only one amino acid molecule, or a multi chain construct comprising more than one amino acid molecule which preferably are covalently connected to each other, for example by disulfide bonds.

In certain embodiments, the antibody or fragment or derivative thereof according to the invention is engineered in such a way that the heavy chain variable region (VH) comprised therein contains at least one CDR which is derived from a different antibody than at least a part of the remaining VH. For example, the VH comprises at least one CDR, preferably two or three CDRs, derived from one antibody, for example a mouse, camel, goat or primate antibody, and at least one FR, preferably two, three or four FRs, derived from another antibody or group of antibodies, preferably antibodies of another species, in particular from human antibodies. In this embodiment, the antibody or fragment or derivative thereof may further comprise a light chain variable region (VL). In particular, the VL may be derived from the antibody from which the one or more CDRs of the VH are derived, or the VL may be a construct wherein one, two or three CDRs are derived from the same antibody as the one or more CDRs of the VH, while one, two, three or preferably all four FRs are derived from the same species, in particular the same antibody or group of antibodies as the one or more FRs of the VH. Moreover, the antibody or fragment or derivative thereof may further comprise one, two, three or four heavy chain constant regions (CH) and/or one light chain constant region (CL) which preferably are derived from the same species, in particular the same antibody or group of antibodies as the FRs of the variable regions. In preferred embodiments, the FRs of the variable regions and the constant regions are not derived from one specific antibody but have an amino acid sequence which represents a consensus sequence or another preferred sequence derived from a specific group of antibodies, for example a group of human antibodies.

In another embodiment, the antibody or fragment or derivative thereof according to the invention is chimeric and comprises one or more heavy chain and optionally light chain variable regions which are derived from one antibody and one or more heavy chain and optionally light chain constant regions which are derived from another antibody. Preferably, the two different antibodies are of different species, such as for example the variable regions are derived from a murine antibody while the constant regions are derived from a human antibody.

The antibody or fragment or derivative thereof according to the invention preferably is glycosylated. In preferred embodiments, it has a human glycosylation pattern, that is, a glycosylation pattern also found on naturally occurring antibodies produced by the human body. Furthermore, the antibody or fragment or derivative thereof may preferably comprise a glycosylation pattern which modulates, in particular enhances one or more activities thereof. For example, the glycosylation pattern may enhance the antibody's, fragment's or derivative's affinity towards its specific epitope, and/or its affinity towards its downstream receptors such as Fc receptors, in particular Fc gamma, Fc alpha or Fc epsilon receptors. Additionally or alternatively, the glycosylation pattern may enhance its complement dependent cytotoxicity (CDC) and/or its antibody-dependent cell-mediated cytotoxicity (ADCC). To this end, the glycosylation pattern of the antibody or fragment or derivative thereof may be engineered or optimized, for example by using specific cell lines which are capable of producing the desired glycosylation pattern. Such cell lines are, for example, K562, KG1, MUTZ-3, NM-F9 [DSM ACC2606], NM-D4 [DSM ACC2605], NM-H9D8 [DSM ACC 2806], NM-H9D8-E6 [DSM ACC 2807], NM H9D8-E6Q12 [DSM ACC 2856], and GT-2X [DSM ACC 2858]. Therefore, the antibody or fragment or derivative thereof preferably has a glycosylation pattern as provided when expressed in one of these cell lines.

The antibody or fragment or derivative thereof according to the invention preferably is useful in medicine, in particular in therapy, diagnosis, prognosis and/or monitoring of a disease, in particular a disease as described herein, preferably cancer.

The heavy chain variable region comprised in the antibody or fragment or derivative thereof according to the invention preferably encompasses at least one CDR selected from the group consisting of CDR1 having the amino acid sequence of SEQ ID NO: 1 or 2, CDR2 having the amino acid sequence of SEQ ID NO: 3 or 4, and CDR3 having the amino acid sequence of SEQ ID NO: 5 or 6, preferably at least CDR1 having the amino acid sequence of SEQ ID NO: 1. In particular, it may comprise a set of CDRs wherein CDR1 has the amino acid sequence of SEQ ID NO: 1, CDR2 has the amino acid sequence of SEQ ID NO: 3 and CDR3 has the amino acid sequence of SEQ ID NO: 5, or wherein CDR1 has the amino acid sequence of SEQ ID NO: 2, CDR2 has the amino acid sequence of SEQ ID NO: 4 and CDR3 has the amino acid sequence of SEQ ID NO: 6.

According to one embodiment, the antibody or fragment or derivative thereof according to the invention preferably comprises a heavy chain variable region having at least one framework region selected from the group consisting of FR1 having the amino acid sequence of SEQ ID NO: 7, in particular SEQ ID NO: 8, FR2 having the amino acid sequence of SEQ ID NO: 9, in particular SEQ ID NO: 10, FR3 having the amino acid sequence of SEQ ID NO: 11, in particular SEQ ID NO: 12, and FR4 having the amino acid sequence of SEQ ID NO: 13, in particular SEQ ID NO: 14. The presence of FR1 having the amino acid sequence of SEQ ID NO: 8 is particularly preferred. The heavy chain variable region thus preferably comprises the amino acid sequence of SEQ ID NO: 15, in particular SEQ ID NO: 16.

In a further embodiment, the antibody or fragment or derivative thereof according to the invention is derived from an antibody comprising one or more of the segments or sequences described above.

The antibody or fragment or derivative thereof according to the invention may further comprise at least one further complementarity determining region selected from the group consisting of CDR1 having the amino acid sequence of SEQ ID NO: 17 or 18, CDR2 having the amino acid sequence of SEQ ID NO: 19 or 20, and CDR3 having the amino acid sequence of SEQ ID NO: 21 or 22, wherein said at least one further complementarity determining region is preferably present within a light chain variable region. In particular, the antibody or fragment or derivative thereof preferably comprises a set of CDRs wherein the CDRs of the heavy chain variable region have the amino acid sequences of SEQ ID NOs: 1, 3 and 5 and the CDRs of the light chain variable region have the amino acid sequences of SEQ ID NOs: 17, 19 and 21, or wherein the CDRs of the heavy chain variable region have the amino acid sequences of SEQ ID NOs: 2, 4 and 6 and the CDRs of the light chain variable region have the amino acid sequences of SEQ ID NOs: 18, 20 and 22. Said light chain variable region preferably comprises the amino acid sequence of SEQ ID NO: 27, in particular SEQ ID NO: 28. In particular preferred embodiments, the antibody according to the invention comprises a VH comprising the amino acid sequence of SEQ ID NO: 16 and a VL comprising the amino acid sequence of SEQ ID NO: 28 or a functional variant or derivative thereof.

According to one embodiment, the antibody comprises the following antibody framework regions (i) FRH1, FRH2, FRH3 and FRH4 for the heavy chain variable region VH have the following amino acid sequences, the amino acid position corresponding to the numeration according to Kabat:

| Pos. | Amino acid |
|---|---|
| for FRH1 (SEQ ID NO: 7) | |
| 1 | E |
| 2 | V |
| 3 | Q or K |
| 4 | L |
| 5 | V |
| 6 | E |
| 7 | S |
| 8 | G |
| 9 | G |
| 10 | G |
| 11 | L |
| 12 | V |
| 13 | Q |
| 14 | P |
| 15 | G |
| 16 | G |
| 17 | S |
| 18 | L or M |
| 19 | R |
| 20 | L |
| 21 | S |
| 22 | C |
| 23 | A or V |
| 24 | A |
| 25 | S |
| 26 | G |
| 27 | F |
| 28 | P |
| 29 | F |
| 30 | S |

-continued

| Pos. | Amino acid |
|---|---|
| for FRH2 (SEQ ID NO: 9) | |
| 36 | W |
| 37 | V |
| 38 | R |
| 39 | Q |
| 40 | A or S |
| 41 | P |
| 42 | G or E |
| 43 | K |
| 44 | G |
| 45 | L |
| 46 | E |
| 47 | W |
| 48 | V |
| 49 | G or A |
| for FRH3 (SEQ ID NO: 11) | |
| 66 | R |
| 67 | F |
| 68 | T |
| 69 | I |
| 70 | S |
| 71 | R |
| 72 | D |
| 73 | D |
| 74 | S |
| 75 | K |
| 76 | N or S |
| 77 | S |
| 78 | L or V |
| 79 | Y |
| 80 | L |
| 81 | Q |
| 82 | M |
| 82a | N |
| 82b | S |
| 82c | L |
| 83 | K |
| 84 | T |
| 85 | E |
| 86 | D |
| 87 | T |
| 88 | A |
| 89 | V |
| 90 | Y |
| 91 | Y |
| 92 | C |
| 93 | T or A |
| 94 | R |
| for FRH4 (SEQ ID NO: 13) | |
| 103 | W |
| 104 | G |
| 105 | Q |
| 106 | G |
| 107 | T |
| 108 | L |
| 109 | V or L |
| 110 | T |
| 111 | V |
| 112 | S |
| 113 | S |

(ii) and optionally FRL1, FRL2, FRL3 and FRL4 for the light chain variable region VL have the following amino acid sequences, the amino acid position corresponding to the numeration according to Kabat:

| Pos. | Amino acid |
|---|---|
| for FRL1 (SEQ ID NO: 23) | |
| 1 | D |
| 2 | I |

| Pos. | Amino acid |
|---|---|
| 3 | V |
| 4 | M |
| 5 | T |
| 6 | Q |
| 7 | S |
| 8 | P |
| 9 | L |
| 10 | S |
| 11 | L or N |
| 12 | P |
| 13 | V |
| 14 | T |
| 15 | P |
| 16 | G |
| 17 | E or D |
| 18 | P |
| 19 | A |
| 20 | S |
| 21 | I |
| 22 | S |
| 23 | C |
| for FRL2 (SEQ ID NO: 24) | |
| 35 | W |
| 36 | Y |
| 37 | L |
| 38 | Q |
| 39 | K |
| 40 | P |
| 41 | G |
| 42 | Q |
| 43 | S |
| 44 | P |
| 45 | Q |
| 46 | L |
| 47 | L |
| 48 | I |
| 49 | Y |
| for FRL3 (SEQ ID NO: 25) | |
| 57 | G |
| 58 | V |
| 59 | P |
| 60 | D |
| 61 | R |
| 62 | F |
| 63 | S |
| 64 | G |
| 65 | S |
| 66 | G |
| 67 | S |
| 68 | G |
| 69 | T |
| 70 | D |
| 71 | F |
| 72 | T |
| 73 | L |
| 74 | K or R |
| 75 | I |
| 76 | S |
| 77 | R |
| 78 | V |
| 79 | E |
| 80 | A |
| 81 | E |
| 82 | D |
| 83 | V |
| 84 | G |
| 85 | V |
| 86 | Y |
| 87 | Y |
| 88 | C |
| for FRL4 (SEQ ID NO: 26) | |
| 98 | F |
| 99 | G |
| 100 | Q or G |
| 101 | G |
| 102 | T |
| 103 | K |
| 104 | V |
| 105 | E |
| 106 | I |
| 107 | K |
| 108 | R |

In certain embodiments, the antibody or fragment or derivative thereof according to the invention is derived from an antibody which does not naturally comprise a proline residue at amino acid position 28, according to the Kabat numbering, of the heavy chain variable region. In particular, FR1 of the heavy chain variable region of the antibody or fragment or derivative thereof according to the invention, comprising amino acid position 28 according to the Kabat numbering, is derived from an antibody which does not comprise a proline residue at position 28 of the VH. Furthermore, also one or more of the remaining FRs and/or one, two or three CDRs of the VH, in particular CDR1, are preferably derived from an antibody which does not comprise a proline residue at position 28 of the VH. The amino acid at position 28 of the VH is then replaced by a proline residue to obtain an antibody or a fragment or derivative thereof according to the invention.

The affinity of the antibody or fragment or derivative thereof according to the invention to the specific antigen preferably is at least as high as the affinity of the antibody or fragment or derivative thereof from which it is derived, in particular an antibody or a fragment or derivative thereof being identical to the antibody or fragment or derivative thereof according to the invention except that it does not comprise a proline residue at amino acid position 28, according to the Kabat numbering, of the heavy chain variable region(s). That is, the antibody or fragment or derivative thereof according to the invention preferably binds to the antigen or epitope with an affinity having a dissociation constant which is equal to or lower than that of said other antibody or fragment or derivative thereof, preferably at least 2-fold lower, at least 3-fold lower, at least 5-fold lower or more preferably at least 10-fold lower.

In one particular embodiment, the antibody or fragment or derivative thereof according to the invention is derived from PankoMab (heavy chain variable region of SEQ ID NO: 29, light chain variable region of SEQ ID NO: 30). PankoMab is a murine monoclonal antibody directed against a glycosylated extracellular epitope in the tandem repeats of MUC1 (Danielczyk, A. et al. (2006) Cancer Immunol. Immunother. 55, 1337-1347).

Furthermore, the antibody according to the invention may comprise at least one heavy chain comprising the amino acid sequence of SEQ ID NO: 31 and optionally at least one light chain comprising the amino acid sequence of SEQ ID NO: 32 or is a fragment or derivative thereof. Preferably, it comprises a set of heavy and light chains comprising the amino acid sequence of SEQ ID NO: 31 and 32, respectively. Said antibody or fragment or derivative thereof may also be a single chain Fv fragment.

In certain embodiments, the engineered antibody or fragment or derivative thereof according to the invention is coupled to a further agent, forming a conjugate. The further agent preferably is useful in therapy, diagnosis, prognosis and/or monitoring of a disease, in particular cancer. For example, the further agent may be selected from the group consisting of antibodies or fragments of antibodies, in particular those of different species and/or different specificity, enzymes, interaction domains, stabilizing domains, signaling sequences, detectable labels, fluorescent dyes, toxins, catalytic antibodies, cytolytic components, immunomodulators, immunoeffectors, MHC class I or class II antigens, chelators for radioactive labeling, radioisotopes, liposomes, transmembrane domains, viruses, and cells. It may be covalently, in particular by fusion or chemical coupling, or non-covalently attached to the antibody or fragment or derivative thereof. A particular preferred further agent is an agent capable of killing cancer cells.

In a further aspect, the present invention provides a nucleic acid encoding the antibody or fragment or derivative thereof according to the invention. The nucleic acid sequence of the nucleic acid according to the invention may have any nucleotide sequence suitable for encoding the antibody or fragment or derivative thereof according to the invention. However, preferably the nucleic acid sequence is at least partially adapted to the specific codon usage of the host cell or organism in which the nucleic acid according to the invention is to be expressed. The nucleic acid according to the invention may be double-stranded or single-stranded DNA or RNA, preferably double-stranded DNA such as cDNA or single-stranded RNA such as mRNA. It may be one consecutive nucleic acid molecule or it may be composed of several nucleic acid molecules, each coding for a different part of the antibody or fragment or derivative thereof according to the invention.

If the antibody or fragment or derivative thereof according to the invention is a single chain construct, the nucleic acid according to the invention preferably is a single nucleic acid molecule containing a coding region which codes for the entire antibody or fragment or derivative thereof. If the antibody or fragment or derivative thereof according to the invention is composed of more than one amino acid chain, the nucleic acid according to the invention may, for example, be a single nucleic acid molecule containing several coding regions each coding for one of the amino acid chains of the antibody or fragment or derivative thereof, preferably separated by regulatory elements such as IRES elements in order to generate separate amino acid chains, or the nucleic acid according to the invention may be composed of several nucleic acid molecules wherein each nucleic acid molecule comprises one or more coding regions each coding for one of the amino acid chains of the antibody or fragment or derivative thereof. In addition to the coding regions encoding the antibody or fragment or derivative thereof according to the invention, the nucleic acid according to the invention may also comprise further nucleic acid sequences or other modifications which, for example, may code for other proteins, may influence the transcription and/or translation of the coding region(s), may influence the stability or other physical or chemical properties of the nucleic acid, or may have no function at all.

In a further aspect, the present invention provides an expression cassette or vector comprising a nucleic acid according to the invention and a promoter operatively connected with said nucleic acid. In addition, the expression cassette or vector may comprise further elements, in particular elements which are capable of influencing and/or regulating the transcription and/or translation of the nucleic acid according to the invention, the amplification and/or reproduction of the expression cassette or vector, the integration of the expression cassette or vector into the genome of a host cell, and/or the copy number of the expression cassette or vector in a host cell. Suitable expression cassettes and vectors comprising respective expression cassettes for expressing antibodies are well known in the art and thus, need no further description here.

Furthermore, the present invention provides a host cell comprising the nucleic acid according to the invention or the expression cassette or vector according to the invention. The host cell according to the invention may be any host cell. It may be an isolated cell or a cell comprised in a tissue. Preferably, the host cell is a cultured cell, in particular a primary cell or a cell of an established cell line, preferably a tumor-derived cell. Preferably, it is a bacterial cell such as *E. coli*, a yeast cell such as a *Saccharomyces* cell, in particular *S. cerevisiae*, an insect cell such as a Sf9 cell, or a mammalian cell, in particular a human cell such as a tumor-derived human cell, a hamster cell such as CHO, or a primate cell. In a preferred embodiment of the invention the host cell is derived from human myeloid leukaemia cells. Preferably, it is selected from the following cells or cell lines: K562, KG1, MUTZ-3, NM-F9 [DSM ACC2606], NM-D4 [DSM ACC2605] or a cell or cell line derived therefrom, or a mixture of cells or cell lines comprising at least one of those aforementioned cells. The host cell is preferably selected from the group consisting of NM-F9 [DSM ACC2606], NM-D4 [DSM ACC2605], NM-H9D8 [DSM ACC 2806], NM-H9D8-E6 [DSM ACC 2807], NM H9D8-E6Q12 [DSM ACC 2856], GT-2X [DSM ACC 2858] and a cell or cell line derived from anyone of said host cells, or a mixture of cells or cell lines comprising at least one of those aforementioned cells. These cell lines were deposited at the DSMZ—Deutsche Sammlung von Mikroorganismen and Zellkulturen, Mascheroder Weg 1b/Inhoffenstraβe 7B, 38124 Braunschweig (DE) under the accession numbers as indicated above. In preferred embodiments, the host cell is optimized for expression of glycoproteins, in particular antibodies, having a specific glycosylation pattern. Preferably, the codon usage in the coding region of the nucleic acid according to the invention and/or the promoter and the further elements of the expression cassette or vector are compatible with and, more preferably, optimized for the type of host cell used. Preferably, the antibody or fragment or derivative thereof according to the invention is produced by a host cell or cell line as described above.

In another aspect, the present invention provides a composition comprising the antibody or fragment or derivative thereof according to the invention, the nucleic acid according to the invention, the expression cassette or vector according to the invention, or the host cell according to the invention. The composition may also contain more than one of these components. Furthermore, the composition may comprise one or more further components selected from the group consisting of solvents, diluents, and excipients. Preferably, the composition is a pharmaceutical composition. In this embodiment, the components of the composition preferably are all pharmaceutically acceptable. The composition may be a solid or fluid composition, in particular a—preferably aqueous—solution, emulsion or suspension or a lyophilized powder.

In a further aspect, the invention provides the antibody or fragment or derivative thereof according to the invention, the nucleic acid according to the invention, the expression cassette or vector according to the invention, the host cell according to the invention, or the composition according to the invention for use in medicine. Preferably, the use in medicine is a use in the treatment, prognosis, diagnosis and/or monitoring of a disease such as, for example, cancer, infectious diseases such as viral and bacterial infections, autoimmune diseases, cardiovascular diseases, inflammatory diseases, macular degeneration, transplant rejection, and multiple sclerosis. In a preferred embodiment, the disease is cancer. Preferably the cancer is selected from the group consisting of cancer of the colon, stomach, liver, pancreas, kidney, blood, lung, and ovary as well as metastases originating therefrom.

For use in the treatment of diseases associated with abnormal cell growth such as cancer, the antibody or fragment or derivative thereof according to the invention may be coupled to a further agent as described above, wherein the further agent preferably is a cytotoxic agent such as a radionuclide or a cytotoxin. Furthermore, the antibody or fragment or derivative thereof may be engineered so as to enhance its ability to activate the patient's immune response, in particular the ability to activate ADCC (antibody-dependent cell-mediated cytotoxicity) and/or CDC (complement dependent cytotoxicity). For example, this may be achieved by optimizing the amino acid sequence and/or the glycosylation pattern of the antibody, in particular of its constant regions.

For use as detection agent in diagnosis, prognosis and/or monitoring of a disease, the antibody or fragment or derivative thereof according to the invention preferably is coupled to a labeling agent which is capable of producing a detectable signal. In particular, said labeling agent may be a radionuclide, a fluorophore or an enzyme.

In another aspect, the invention provides a method for improving the antigen binding and/or recognition of an antibody or a fragment or derivative thereof which is capable of binding to a mucin protein and which comprises a heavy chain variable region, comprising the step of providing a proline residue at position 28, according to the Kabat numbering, of the heavy chain variable region.

In preferred embodiments, the proline residue at position 28 is obtained by altering the sequence of the nucleic acid encoding the antibody or fragment or derivative thereof. In particular, the nucleic acid sequence is altered by introducing a mutation in the codon coding for said amino acid residue. Depending on the amino acid residue which is to be replaced, only one nucleotide, two nucleotides or all three nucleotides of said codon are replaced so that a codon coding for a proline residue is obtained. According to the universal genetic code, codons CCA, CCG, CCC, CCU and CCT encode the amino acid proline. Thus, the nucleic acid coding for the antibody or fragment or derivative thereof should be altered, in particular mutated, in such a manner that the codon encoding amino acid number 28 of the VH has a nucleic acid sequence selected from the group consisting of CCA, CCG, CCC, CCU and CCT. The antibody or fragment or derivative thereof wherein the amino acid at position 28 of the VH is replaced by a proline residue is then obtained by expressing said altered nucleic acid in a suitable expression system.

The codon of amino acid residue 28 of the VH in the nucleic acid coding for the antibody or fragment or derivative thereof may be altered to obtain a codon coding for proline by any method known in the art. In particular, it may be altered by specific or random mutation as well as directed mutation such as affinity maturation. For example, an oligonucleotide primer complementary to a part of the nucleic acid encoding the antibody or fragment or derivative thereof and carrying the desired mutation may be used in a reaction for amplifying said nucleic acid, in particular a PCR-based amplification reaction.

However, also any other known method for providing a proline residue in a protein may be used. In particular, chemical synthesis of the protein having the altered amino acid sequence or chemical modification of the protein may be used.

By providing a proline residue at position 28 of the VH, the antigen binding and/or antigen recognition properties of the antibody or fragment or derivative thereof is improved. Improving the antigen binding and/or antigen recognition of the antibody or fragment or derivative thereof in particular includes enhancing the affinity to its antigen and/or increasing the specificity towards its antigen. In particular, the antibody or fragment or derivative thereof, after providing a proline residue at position 28 of the VH, has improved antigen binding and/or antigen recognition properties compared to an identical antibody or fragment or derivative thereof not having a proline residue at amino acid position 28 of the VH.

Enhancing the affinity in this respect preferably refers to a lowering of the dissociation constant of the binding of the antibody to its specific antigen or epitope. Preferably, the dissociation constant is lowered at least 1.2-fold, more preferably at least 1.3-fold, at least 1.5-fold, at least 1.7-fold, at least 2-fold, at least 3-fold, at least 5-fold, at least 10-fold, and most preferably at least 50-fold or at least 100-fold. Increasing the specificity in this respect preferably refers to an increase in the difference of the affinity of the antigen towards its specific antigen or epitope compared to its affinity towards any other molecule which is commonly present along with the specific antigen or epitope. Preferably, the difference in the dissociation constants of these two affinities is increased at least 1.2-fold, more preferably at least 1.3-fold, at least 1.5-fold, at least 1.7-fold, at least 2-fold, at least 3-fold, at least 5-fold, at least 10-fold, and most preferably at least 50-fold or at least 100-fold.

The mucin antigen recognized by the antibody or fragment or derivative thereof preferably is a tumor-associated antigen, i.e. an antigen which may be used for discriminating tumor tissue from normal tissue and/or as marker for specifically targeting therapeutic agents to tumor tissue. By providing a proline residue at position 28 of the VH, the usefulness in medicine of the antibody or fragment or derivative thereof preferably may be improved, for example by enhancing the ability to discriminate between tumor tissue and normal tissue and/or lowering the concentration of the antibody or antibody-containing conjugate necessary for achieving the desired medicinal effect.

The antibody or fragment or derivative thereof which antigen binding and/or recognition is to be improved by the method according to the invention may not comprise a proline residue at position 28, according to the Kabat numbering, of at least one heavy chain variable region. Furthermore, the embodiments or features described above with respect to the antibody or fragment or derivative thereof according to the invention also apply, alone or in the various possible combinations, to the antibody or fragment or derivative thereof which antigen binding and/or recognition is to be improved by the method according to the invention. In particular, the antibody or fragment or derivative thereof which antigen binding and/or recognition is to be improved may have any of the amino acid sequences or combinations of amino acid sequences described above, wherein, however, the amino acid residue at position 28, according to the Kabat numbering, of at least one heavy chain variable region is an amino acid residue other than proline.

Preferably, the antibody or fragment or derivative thereof which antigen binding and/or recognition is to be improved by the method according to the invention is capable of specifically binding to MUC1, in particular an epitope on the extracellular tandem repeats of MUC1, preferably in a conformation-dependent and/or glycosylation-dependent manner. Specific embodiments of the epitope or antigen are described above with respect to the antigen or fragment or derivative according to the invention. In particularly preferred embodiments, the heavy chain variable region of the antibody or fragment or derivative thereof which antigen binding and/or recognition is to be improved by the method according to the invention comprises (i) one or more, preferably all of the CDRs of the group consisting of CDR1 having SEQ ID NO: 1, CDR2 having SEQ ID NO: 3 and CDR3 having SEQ ID NO: 5, or one or more, preferably all of the CDRs of the group consisting of CDR1 having SEQ ID NO: 2, CDR2 having SEQ ID NO: 4 and CDR3 having SEQ ID NO: 6, in particular preferably at least CDR1 having SEQ ID NO: 1; and/or (ii) one or more, preferably all of the FRs of the group consisting of FR1 having SEQ ID NO: 33 or 34, FR2 having SEQ ID NO: 9 or 35, FR3 having SEQ ID NO: 11 or 36, FR4 having SEQ ID NO: 13 or 37, in particular preferably at least FR1 having SEQ ID NO: 33.

Preferably, the heavy chain variable region comprises the amino acid sequence of SEQ ID NO: 38 or 29. Furthermore, the antibody which antigen binding and/or recognition is to be improved may comprise one or more heavy chains comprising the amino acid sequence of SEQ ID NO: 39, and/or one or more light chains comprising the amino acid sequence of SEQ ID NO: 32. Preferably, it comprises at least one pair of heavy and light chains comprising the amino acid sequence of SEQ ID NO: 39 and 32, respectively, or is a functional fragment or derivative of the foregoing. Alternatively, a single chain Fv fragment may be used in the method according to the invention. In particularly preferred embodiments, PankoMab or an antibody or fragment derived therefrom, or an antibody or fragment thereof exhibiting cross-specificity with PankoMab are used in the method according to the invention.

The antibody or fragment or derivative thereof according to the invention may be obtainable or prepared by the method for improving the antigen binding and/or recognition of an antibody or a fragment or derivative thereof according to the invention.

Furthermore, the present invention provides a method for preparing a nucleic acid according to the invention, comprising the steps of (a) providing a nucleic acid comprising the nucleic acid sequence of an antibody or a fragment or derivative thereof which does not comprise a proline residue at amino acid position 28, according to the Kabat numbering, of the heavy chain variable region; and (b) introducing a mutation into the codon coding for amino acid number 28, according to the Kabat numbering, of the heavy chain variable region so that said codon codes for a proline residue.

The mutation may be introduced by any method appropriate for this purpose. A variety of suitable methods are known in the art. For example, the mutation may be introduced by random or directed mutation of the initial nucleic acid, for example using an oligonucleotide primer carrying the mutation in a PCR-based method. Alternatively, the nucleic acid or a part thereof containing the mutation may be chemically synthesized and ligated to the remaining part of the nucleic acid, where appropriate.

Furthermore, a method for preparing the engineered antibody or fragment or derivative thereof according to the invention may be based on the above method for preparing a nucleic acid according to the invention. Said method for preparing the engineered antibody or fragment or derivative thereof according to the invention comprises the steps (a) and (b) of the method for preparing a nucleic acid according to the invention and further comprises the step of expressing the nucleic acid obtained in step (b) in an expression system, thereby generating the antibody or fragment or derivative thereof according to the invention encoded by said nucleic acid.

Appropriate expression systems may be cell-free expression systems or expression systems based on the host cells described above. In particular, the use of mammalian host cells is preferred, especially the use of human host cells, preferably host cells as disclosed above. Preferably, the host cell used for expressing the antibody or fragment or derivative thereof is optimized with respect to the glycosylation pattern of the antibody expressed by the host cell.

The features disclosed with respect to the other aspects of the present invention, in particular with the antibody according to the invention, the nucleic acid according to the invention, the expression cassette, vector or host cell according to the invention, or the method for improving the antigen binding and/or recognition of an antibody or a fragment or derivative thereof according to the invention, alone or in combination, may also be applied to the method for preparing a nucleic acid according to the invention.

FIGURES

FIG. 1 shows the binding of the chimeric mouse/human and several humanized PankoMab-derived antibodies to a glycosylated (256.1) and a non-glycosylated (258.1) 30-mer polypeptide comprising the MUC1 epitope of PankoMab, and to different glycosylated polypeptides comprising 2, 4 or 5 MUC1 tandem repeats (TR2, TR4 and TR5, respectively). Binding to BSA was used as control. The experiments were done with different dilutions of cell supernatants containing antibodies after adjustment of the titers (indicated on the left of the graphs).

Figure 2:
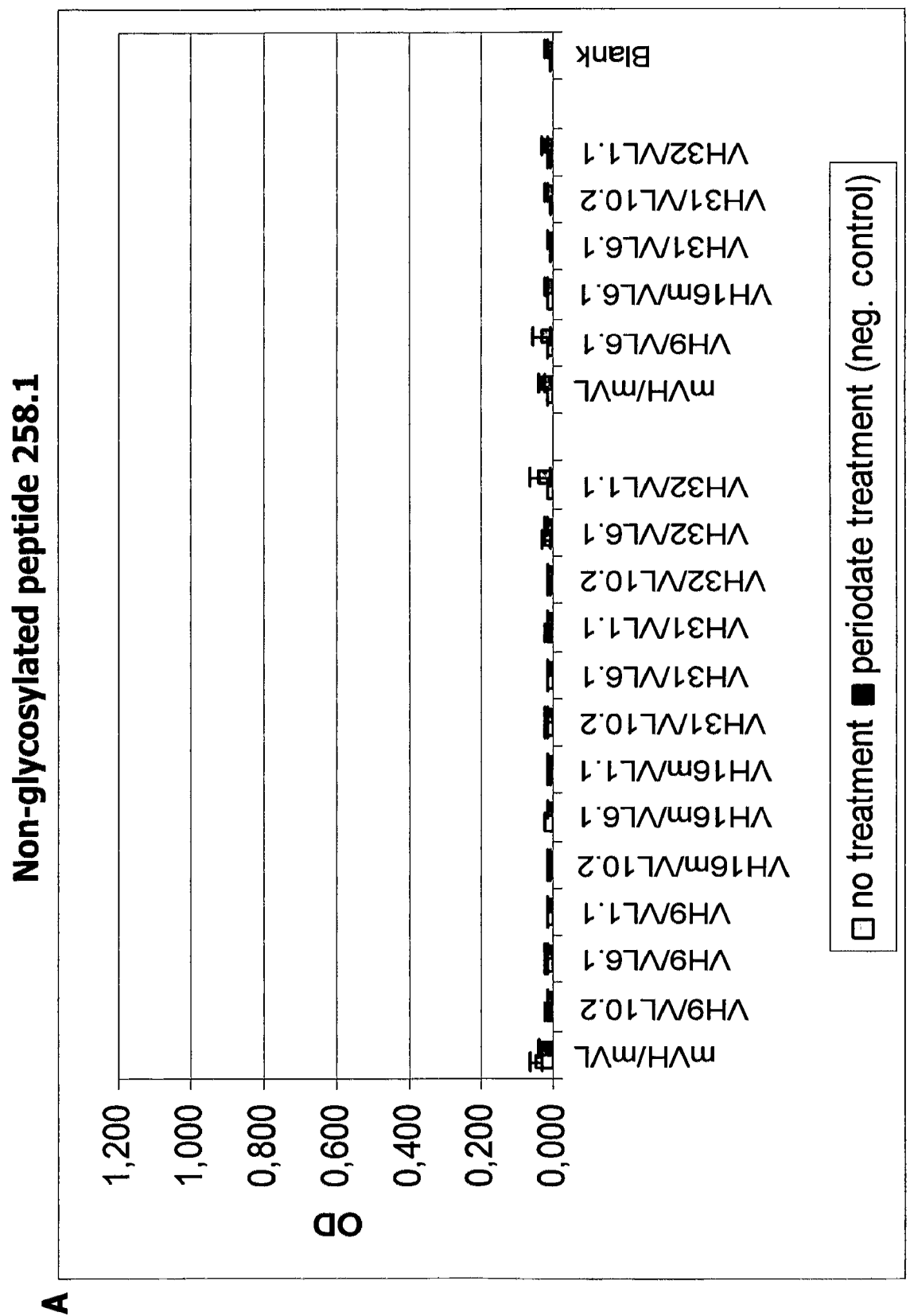
Figure 2:
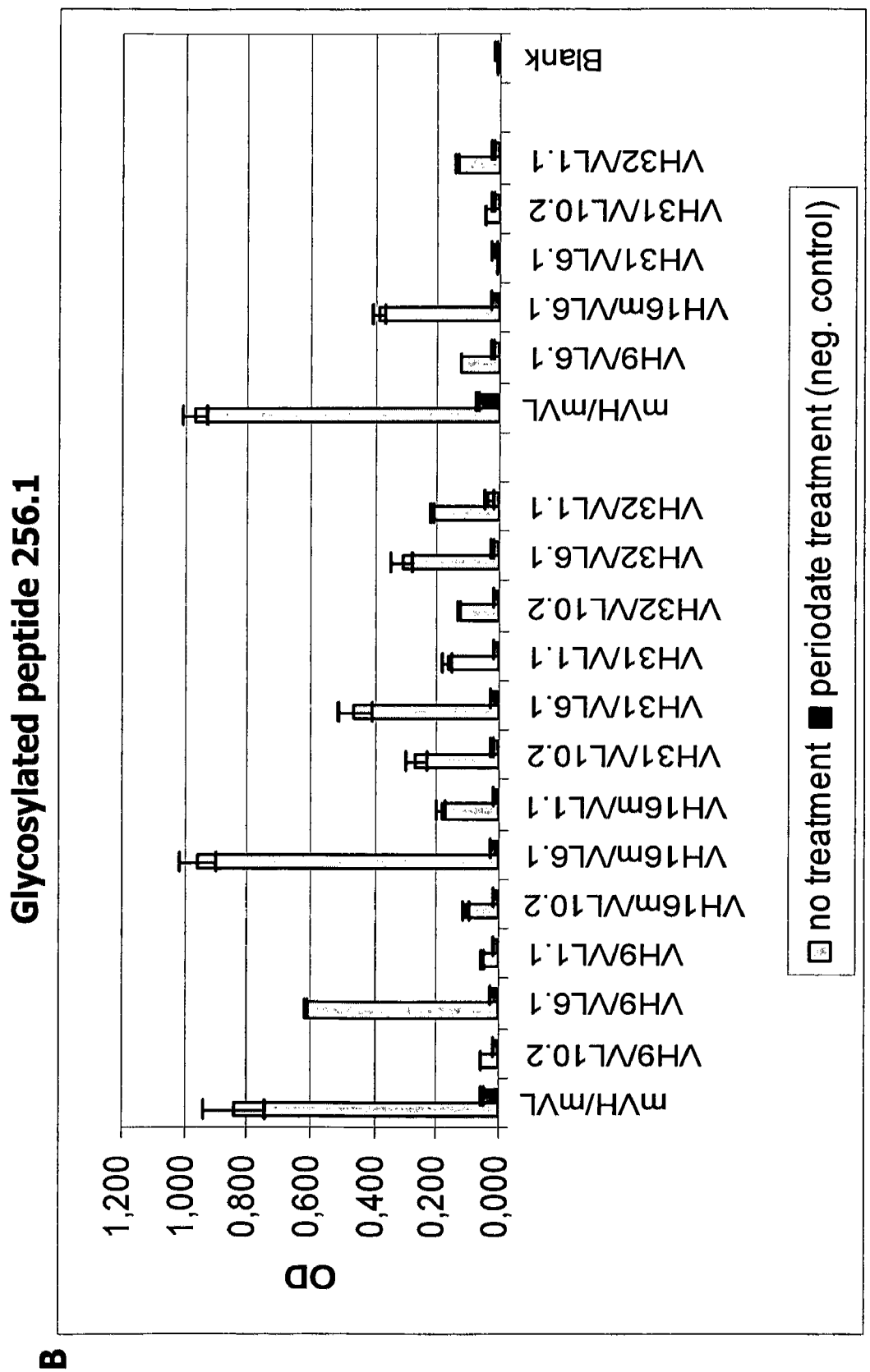

FIG. 2 shows the binding of the chimeric mouse/human and several humanized PankoMab-derived antibodies to (A) a non-glycosylated (258.1) and (B) a glycosylated (256.1) 30-mer polypeptide comprising the MUC1 epitope of PankoMab. As control (blank), no primary antibody was used. As further control, the experiments were also done after treatment of the 30-mer polypeptides with periodate (with PO) which breaks up the saccharide rings and thus, destroys the glycosylation of the polypeptide 256.1.

Figure 3:
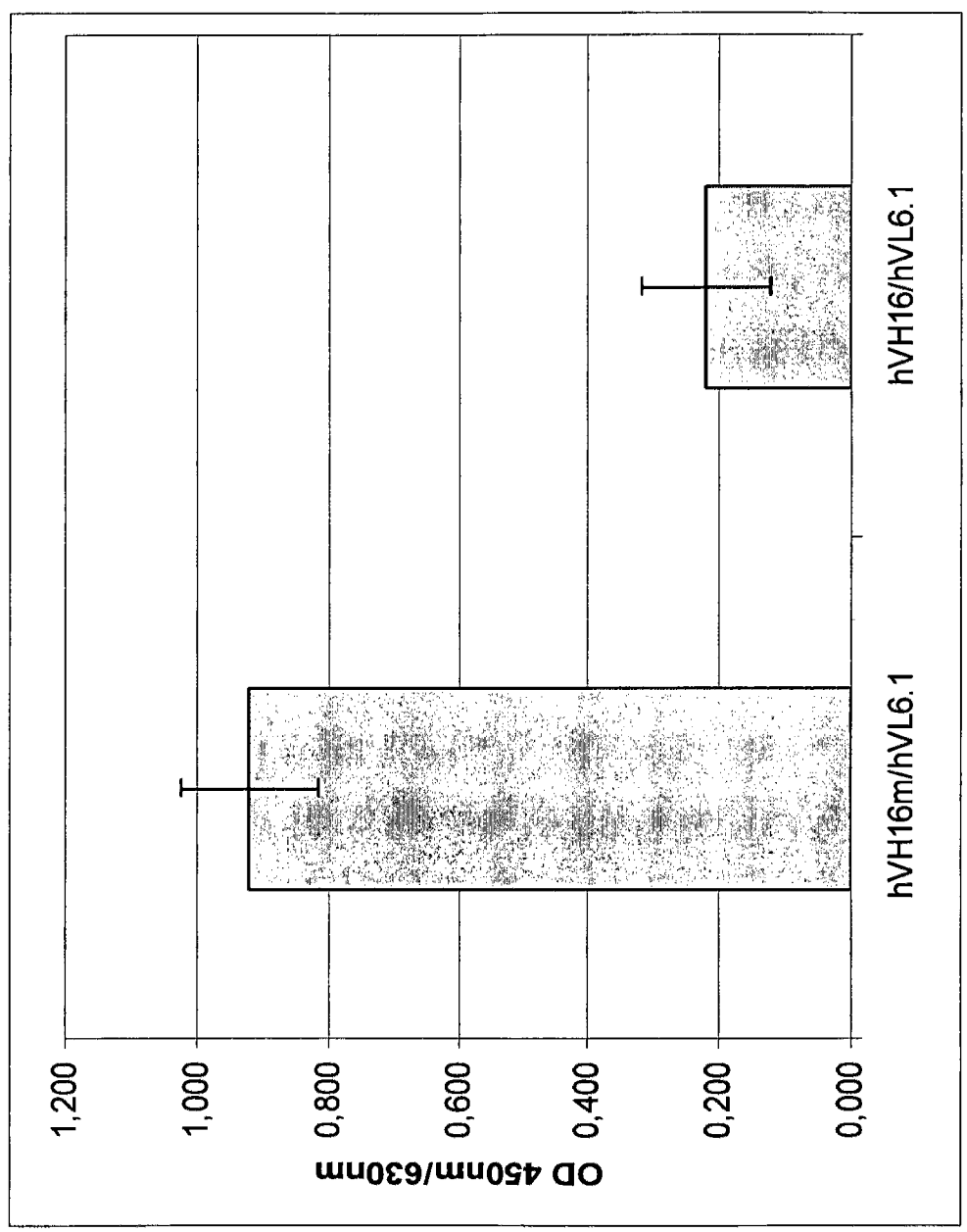

FIG. 3 shows a direct comparison of the binding of the VH16m/VL6.1 antibody (having a proline residue at position 28 of the heavy chain variable region) and the VH16/VL6.1 antibody (having a threonine residue at position 28 of the heavy chain variable region) to the glycosylated 30-mer target peptide 256.1 comprising the MUC1 epitope of PankoMab.

EXAMPLES

Example 1

Humanization of the Murine Heavy and Light Chain Variable Regions of PankoMab

PankoMab is a monoclonal antibody directed against a glycosylated, tumor-associated epitope in the extracellular tandem repeats of human MUC1. After preparation of the murine antibody PankoMab (Danielczyk, A. et al. (2006) Cancer Immunol. Immunother. 55, 1337-1347), the nucleic acid sequences coding for the heavy and light chain variable regions (VH and VL) were ligated to the genomic sequences of the human constant γ1 region (CH) and the human constant κ region (CL), respectively. For a detailed description of this cloning procedure it is referred to WO 2004/065423 A2, in particular example 3.

On the basis of these chimeric clones (heavy chain: SEQ ID NO: 40, light chain: SEQ ID NO: 41), humanized PankoMab antibodies were constructed. To this end, point mutations were introduced into the nucleic acid sequences of the murine framework regions of VH and VL in order to generate the corresponding human framework regions. The target human framework regions were selected from a human germ line antibody library. In particular, the most related framework regions were chosen from the library depending on their overall sequence similarity and their CDR loop classification. Then, human consensus sequences for the heavy and light chain variable regions were used to identify unusual amino acids. All data obtained were considered to design a set of different variable sequences of humanized variable light (10 variants) and variable heavy chains (15 variants). Variants contain back-mutations to the murine sequence on critical positions and/or mutations of rare amino acids, i.e. amino acids which are rather uncommon on their specific position in human framework regions, to their common counterparts. Following expression of the different constructs humanized antibody variants were screened in a 256.1-specific ELISA and the best binders were selected.

By the above described method, the following humanized antibody heavy and light chains variable regions were obtained and characterized further.

TABLE 1

| heavy chain variable region | SEQ ID | light chain variable region | SEQ ID |
|---|---|---|---|
| mVH | 29 | mVL | 30 |
| VH1 | 38 | VL1.1 | 46 |
| VH9 | 42 | VL6.1 | 28 |
| VH16 | 43 | VL10.1 | 47 |
| VH16m | 16 | VL10.2 | 48 |
| VH31 | 44 | | |
| VH32 | 45 | | | mVH and mVL represent the murine heavy and light chain variable regions, respectively, which were used as basis for the humanization.

Example 2

Affinity of the Humanized PankoMab Variants to the Glycosylated and Non-Glycosylated Epitope Using IgG antibodies comprising these heavy and light chain variable regions in different combinations, two binding assays with a 30-mer polypeptide containing the epitope of PankoMab (peptide 258.1: APPAHGVTSAPDTRPAPG-STAPPAHGVTSA, SEQ ID NO: 51) were done, wherein in one assay the peptide was glycosylated at the central threonine with N-acetyl galactosamine (peptide 256.1: APPAH-GVTSAPDT[GalNAcα]RPAPGSTAPPAHGVTSA) while in the other assay the peptide was non-glycosylated. Furthermore, binding assays with multiple TN-glycosylated MUC1 tandem repeats containing 2, 4 or 5 tandem repeats (TR2, TR4 and TR5: SEQ ID NOs: 52, 53 and 54, respectively) were performed.

The results of these assays are shown in FIGS. 1 and 2. Using these assays, it could be demonstrated that antibodies containing the heavy chain variable region VH16m having an unusual proline residue at position 28 have a higher affinity towards the glycosylated epitope-containing polypeptide than those not having a proline residue at position 28 of the heavy chain variable region.

The direct comparison of two humanized anti-MUC1 antibodies which only differ in the amino acid residue at position 28 of the heavy chain variable region, once being proline (heavy chain variable region VH16m, light chain variable region VL6.1) and once being threonine (heavy chain variable region VH16, light chain variable region VL6.1), demonstrates that this amino acid exchange is responsible for the improved binding to the glycosylated epitope-containing target peptide 256.1 (see FIG. 3).

Identification of the Deposited Biological Material

The cell lines DSM ACC 2606 and DSM ACC 2605 were deposited at the DSMZ—Deutsche Sammlung von Mikroorganismen und Zellkulturen GmbH, Mascheroder Weg 1b, 38124 Braunschweig (DE) by Nemod Biotherapeutics GmbH & Co. KG, Robert-Rössle-Str. 10, 13125 Berlin (DE). Glycotope is entitled to refer to these biological materials since they were in the meantime assigned from Nemod Biotherapeutics GmbH & Co. KG to Glycotope GmbH.

The cell lines DSM ACC 2806, DSM ACC 2807, DSM ACC 2856 and DSM ACC 2858 were deposited at the DSMZ—Deutsche Sammlung von Mikroorganismen und Zellkulturen GmbH, Inhoffenstraße 7B, 38124 Braunschweig (DE) by Glycotope GmbH, Robert-Rössle-Str. 10, 13125 Berlin (DE).

| Accession Number | Name of the Cell Line | Depositor | Date of Deposition |
|---|---|---|---|
| DSM ACC 2606 | NM-F9 | Nemod Biotherapeutics | Aug. 14, 2003 |
| DSM ACC 2605 | NM-D4 | Nemod Biotherapeutics | Aug. 14, 2003 |
| DSM ACC 2806 | NM-H9D8 | Glycotope GmbH | Sep. 15, 2006 |
| DSM ACC 2807 | NM-H9D8-E6 | Glycotope GmbH | Oct. 5, 2006 |
| DSM ACC 2856 | NM-H9D8-E6Q12 | Glycotope GmbH | Aug. 8, 2007 |
| DSM ACC 2858 | GT-2x | Glycotope GmbH | Sep. 7, 2007 |

| Applicant's or agent's file reference 51 878 K | International application No. |
|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description on page 15 , line 35 .

B. IDENTIFICATION OF DEPOSIT — Further deposits are identified on an additional sheet ☒

Name of depositary institution
Deutsche Sammlung von Mikroorganismen und Zellkulturen (DSMZ)

Address of depositary institution *(including postal code and country)*
Mascheroder Weg 1b
38124 Braunschweig
DE

| Date of deposit | Accession Number |
|---|---|
| 2003-08-14 | DSM ACC2606 |

C. ADDITIONAL INDICATIONS *(leave blank if not applicable)* This information is continued on an additional sheet ☒

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July1998; reprint January 2004)

Additional Indications According to Form PCT/RO/134 for Accession Number DSM ACC2606:

Applicant herewith requests for those countries which have a respective provision that the furnishing of a sample of the deposited material referred to in the application may only be made to an independent, nominated expert (request of the "expert solution" where applicable, in particular in Australia, Canada, Croatia, Denmark, Finland, Germany, Iceland, Norway, Singapore, Spain, Sweden, United Kingdom, Europe).

For Europe, applicant accordingly requests that a sample of the deposited biological material will be made available as provided in Rule 33(1)(2) EPC until the publication of the mention of the grant of the patent or for 20 years from the date of filing if the application is refused or withdrawn or deemed to be withdrawn, only by the issue of a sample to an expert nominated by the person requesting the sample (Rule 32 EPC).

BUDAPEST TREATY ON THE INTERNATIONAL
RECOGNITION OF THE DEPOSIT OF MICROORGANISMS
FOR THE PURPOSES OF PATENT PROCEDURE

DSMZ
Deutsche Sammlung von
Mikroorganismen und
Zellkulturen GmbH

INTERNATIONAL FORM

Nemod Biotherapeutics GmbH & Co. KG
Robert-Rössle-Str. 10
13125 Berlin

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: NM-F9 | Accession number given by the INTERNATIONAL DEPOSITARY AUTHORITY: DSM ACC2606 |

| II. SCIENTIFIC DESCRIPTION AND/OR PROPOSED TAXONOMIC DESIGNATION |
|---|
| The microorganism identified under I. above was accompanied by: <br><br> ( x ) a scientific description <br> ( ) a proposed taxonomic designation <br><br> (Mark with a cross where applicable). |

| III. RECEIPT AND ACCEPTANCE |
|---|
| This International Depositary Authority accepts the microorganism identified under I. above, which was received by it on 2003-08-14 (Date of the original deposit)¹. |

| IV. RECEIPT OF REQUEST FOR CONVERSION |
|---|
| The microorganism identified under I above was received by this International Depositary Authority on (date of original deposit) and a request to convert the original deposit to a deposit under the Budapest Treaty was received by it on (date of receipt of request for conversion). |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH <br><br> Address: Mascheroder Weg 1b <br> D-38124 Braunschweig | Signature(s) of person(s) having the power to represent the International Depositary Authority or of authorized official(s): <br><br> Date: 2003-10-16 |

¹ Where Rule 6.4 (d) applies, such date is the date on which the status of international depositary authority was acquired.

Form DSMZ-BP/4 (sole page) 12/2001

| Applicant's or agent's file reference 51 878 K | International application No. |
|---|---|

INDICATIONS RELATING TO DEPOSITED MICROORGANISM OR OTHER BIOLOGICAL MATERIAL (PCT Rule 13bis)

| A. The indications made below relate to the deposited microorganism or other biological material referred to in the description on page 15, line 36 |
|---|
| B. IDENTIFICATION OF DEPOSIT    Further deposits are identified on an additional sheet [X] |
| Name of depositary institution<br>Deutsche Sammlung von Mikroorganismen und Zellkulturen (DSMZ) |
| Address of depositary institution (including postal code and country)<br>Mascheroder Weg 1b<br>38124 Braunschweig<br>DE |

| Date of deposit<br>2003-08-14 | Accession Number<br>DSM ACC2605 |
|---|---|

| C. ADDITIONAL INDICATIONS (leave blank if not applicable)    This information is continued on an additional sheet [X] |
|---|
| |

| D. DESIGNATED STATES FOR WHICH INDICATIONS ARE MADE (if the indications are not for all designated States) |
|---|
| |

| E. SEPARATE FURNISHING OF INDICATIONS (leave blank if not applicable) |
|---|
| The indications listed below will be submitted to the International Bureau later (specify the general nature of the indications e.g., "Accession Number of Deposit") |

| For receiving Office use only | For International Bureau use only |
|---|---|
| [ ] This sheet was received with the international application | [ ] This sheet was received by the International Bureau on: |
| Authorized officer | Authorized officer |

Form PCT/RO/134 (July1998; reprint January 2004)

Additional Indications According to Form PCT/RO/134 for Accession Number DSM ACC2605:

Applicant herewith requests for those countries which have a respective provision that the furnishing of a sample of the deposited material referred to in the application may only be made to an independent, nominated expert (request of the "expert solution" where applicable, in particular in Australia, Canada, Croatia, Denmark, Finland, Germany, Iceland, Norway, Singapore, Spain, Sweden, United Kingdom, Europe).

For Europe, applicant accordingly requests that a sample of the deposited biological material will be made available as provided in Rule 33(1)(2) EPC until the publication of the mention of the grant of the patent or for 20 years from the date of filing if the application is refused or withdrawn or deemed to be withdrawn, only by the issue of a sample to an expert nominated by the person requesting the sample (Rule 32 EPC).

| Applicant's or agent's file reference 51 878 K | International application No. |
|---|---|

INDICATIONS RELATING TO DEPOSITED MICROORGANISM OR OTHER BIOLOGICAL MATERIAL (PCT Rule 13bis)

| A. The indications made below relate to the deposited microorganism or other biological material referred to in the description on page 15 , line 36 . |
|---|

| B. IDENTIFICATION OF DEPOSIT | Further deposits are identified on an additional sheet [X] |
|---|---|
| Name of depositary institution<br>Deutsche Sammlung von Mikroorganismen und Zellkulturen (DSMZ) | |
| Address of depositary institution *(including postal code and country)*<br>Inhoffenstr. 7B<br>38124 Braunschweig<br>DE | |

| Date of deposit<br>2006-09-15 | Accession Number<br>DSM ACC2806 |
|---|---|

| C. ADDITIONAL INDICATIONS *(leave blank if not applicable)*    This information is continued on an additional sheet [X] |
|---|
| |

| D. DESIGNATED STATES FOR WHICH INDICATIONS ARE MADE *(if the indications are not for all designated States)* |
|---|
| |

| E. SEPARATE FURNISHING OF INDICATIONS *(leave blank if not applicable)* |
|---|
| The indications listed below will be submitted to the International Bureau later *(specify the general nature of the indications e.g., "Accession Number of Deposit")* |

| For receiving Office use only | For International Bureau use only |
|---|---|
| ☐ This sheet was received with the international application | ☐ This sheet was received by the International Bureau on: |
| Authorized officer | Authorized officer |

Form PCT/RO/134 (July1998; reprint January 2004)

Additional Indications According to Form PCT/RO/134 for Accession Number DSM ACC2806:

Applicant herewith requests for those countries which have a respective provision that the furnishing of a sample of the deposited material referred to in the application may only be made to an independent, nominated expert (request of the "expert solution" where applicable, in particular in Australia, Canada, Croatia, Denmark, Finland, Germany, Iceland, Norway, Singapore, Spain, Sweden, United Kingdom, Europe).

For Europe, applicant accordingly requests that a sample of the deposited biological material will be made available as provided in Rule 33(1)(2) EPC until the publication of the mention of the grant of the patent or for 20 years from the date of filing if the application is refused or withdrawn or deemed to be withdrawn, only by the issue of a sample to an expert nominated by the person requesting the sample (Rule 32 EPC).

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Glycotope GmbH

Robert-Rössle-Str. 10

13125 Berlin

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR: <br> NM-H9D8 | Accession number given by the INTERNATIONAL DEPOSITARY AUTHORITY: <br><br> DSM ACC2806 |

| II. SCIENTIFIC DESCRIPTION AND/OR PROPOSED TAXONOMIC DESIGNATION |
|---|
| The microorganism identified under I. above was accompanied by: <br><br> ( ) a scientific description <br> ( ) a proposed taxonomic designation <br><br> (Mark with a cross where applicable). |

| III. RECEIPT AND ACCEPTANCE |
|---|
| This International Depositary Authority accepts the microorganism identified under I. above, which was received by it on 2006-09-15 (Date of the original deposit)¹. |

| IV. RECEIPT OF REQUEST FOR CONVERSION |
|---|
| The microorganism identified under I. above was received by this International Depositary Authority on                                               (date of original deposit) <br> and a request to convert the original deposit to a deposit under the Budapest Treaty was received by it on          (date of receipt of request) <br> for conversion). |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH <br><br> Address: Inhoffenstr. 7 B <br> D-38124 Braunschweig | Signature(s) of person(s) having the power to represent the International Depositary Authority or of authorized official(s): <br><br> *V. Weihs* <br><br> Date: 2006-10-09 |

¹ Where Rule 6.4 (d) applies, such date is the date on which the status of international depositary authority was acquired.

Form DSMZ-BP/4 (sole page) 08/2006

| Applicant's or agent's file reference 51 878 K | International application No. |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 15, line 36.

B. IDENTIFICATION OF DEPOSIT  Further deposits are identified on an additional sheet [X]

Name of depositary institution
Deutsche Sammlung von Mikroorganismen und Zellkulturen (DSMZ)

Address of depositary institution (including postal code and country)
Inhoffenstr. 7B
38124 Braunschweig
DE

| Date of deposit 2006-10-05 | Accession Number DSM ACC2807 |
|---|---|

C. ADDITIONAL INDICATIONS (leave blank if not applicable)    This information is continued on an additional sheet [X]

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

---

For receiving Office use only
[ ] This sheet was received with the international application Authorized officer For International Bureau use only
[ ] This sheet was received by the International Bureau on:

Authorized officer

Form PCT/RO/134 (July1998; reprint January 2004)

Additional Indications According to Form PCT/RO/134 for Accession Number DSM ACC2807:

Applicant herewith requests for those countries which have a respective provision that the furnishing of a sample of the deposited material referred to in the application may only be made to an independent, nominated expert (request of the "expert solution" where applicable, in particular in Australia, Canada, Croatia, Denmark, Finland, Germany, Iceland, Norway, Singapore, Spain, Sweden, United Kingdom, Europe).

For Europe, applicant accordingly requests that a sample of the deposited biological material will be made available as provided in Rule 33(1)(2) EPC until the publication of the mention of the grant of the patent or for 20 years from the date of filing if the application is refused or withdrawn or deemed to be withdrawn, only by the issue of a sample to an expert nominated by the person requesting the sample (Rule 32 EPC).

BUDAPEST TREATY ON THE INTERNATIONAL
RECOGNITION OF THE DEPOSIT OF MICROORGANISMS
FOR THE PURPOSES OF PATENT PROCEDURE

INTERNATIONAL FORM

Glycotope GmbH
Robert-Rössle-Str. 10
13125 Berlin

RECEIPT IN THE CASE OF AN ORIGINAL DEPOSIT
issued pursuant to Rule 7.1 by the
INTERNATIONAL DEPOSITARY AUTHORITY
identified at the bottom of this page

| I. IDENTIFICATION OF THE MICROORGANISM | |
|---|---|
| Identification reference given by the DEPOSITOR:<br>NM-H9D8-E6 | Accession number given by the<br>INTERNATIONAL DEPOSITARY AUTHORITY:<br>DSM ACC2807 |

| II. SCIENTIFIC DESCRIPTION AND/OR PROPOSED TAXONOMIC DESIGNATION |
|---|
| The microorganism identified under I. above was accompanied by:<br>( ) a scientific description<br>( ) a proposed taxonomic designation<br>(Mark with a cross where applicable). |

| III. RECEIPT AND ACCEPTANCE |
|---|
| This International Depositary Authority accepts the microorganism identified under I. above, which was received by it on 2006-10-05 (Date of the original deposit). |

| IV. RECEIPT OF REQUEST FOR CONVERSION |
|---|
| The microorganism identified under I above was received by this International Depositary Authority on (date of original deposit) and a request to convert the original deposit to a deposit under the Budapest Treaty was received by it on (date of receipt of request for conversion). |

| V. INTERNATIONAL DEPOSITARY AUTHORITY | |
|---|---|
| Name: DSMZ-DEUTSCHE SAMMLUNG VON MIKROORGANISMEN UND ZELLKULTUREN GmbH<br>Address: Inhoffenstr. 7 B<br>D-38124 Braunschweig | Signature(s) of person(s) having the power to represent the International Depositary Authority or of authorized official(s):<br><br>Date: 2006-10-18 |

[1] Where Rule 6.4 (d) applies, such date is the date on which the status of international depositary authority was acquired.

Form DSMZ-BP/4 (sole page) 08/2006

| Applicant's or agent's file reference 51 878 K | International application No. |
|---|---|

INDICATIONS RELATING TO DEPOSITED MICROORGANISM OR OTHER BIOLOGICAL MATERIAL (PCT Rule 13*bis*)

A. The indications made below relate to the deposited microorganism or other biological material referred to in the description
on page 15, line 37.

B. IDENTIFICATION OF DEPOSIT     Further deposits are identified on an additional sheet [X]

Name of depositary institution
Deutsche Sammlung von Mikroorganismen und Zellkulturen (DSMZ)

Address of depositary institution *(including postal code and country)*
Inhoffenstr. 7B
38124 Braunschweig
DE

| Date of deposit | Accession Number |
|---|---|
| 2007-08-08 | DSM ACC2856 |

C. ADDITIONAL INDICATIONS *(leave blank if not applicable)*     This information is continued on an additional sheet [X]

D. DESIGNATED STATES FOR WHICH INDICATIONS ARE MADE *(if the indications are not for all designated States)*

E. SEPARATE FURNISHING OF INDICATIONS *(leave blank if not applicable)*

The indications listed below will be submitted to the International Bureau later *(specify the general nature of the indications e.g., "Accession Number of Deposit")*

| For receiving Office use only | For International Bureau use only |
|---|---|
| [ ] This sheet was received with the international application | [ ] This sheet was received by the International Bureau on: |
| Authorized officer | Authorized officer |

Form PCT/RO/134 (July1998; reprint January 2004)

Additional Indications According to Form PCT/RO/134 for Accession Number DSM ACC2856:

Applicant herewith requests for those countries which have a respective provision that the furnishing of a sample of the deposited material referred to in the application may only be made to an independent, nominated expert (request of the "expert solution" where applicable, in particular in Australia, Canada, Croatia, Denmark, Finland, Germany, Iceland, Norway, Singapore, Spain, Sweden, United Kingdom, Europe).

For Europe, applicant accordingly requests that a sample of the deposited biological material will be made available as provided in Rule 33(1)(2) EPC until the publication of the mention of the grant of the patent or for 20 years from the date of filing if the application is refused or withdrawn or deemed to be withdrawn, only by the issue of a sample to an expert nominated by the person requesting the sample (Rule 32 EPC).

| Applicant's or agent's file reference 51 878 K | International application No. |
|---|---|

INDICATIONS RELATING TO DEPOSITED MICROORGANISM OR OTHER BIOLOGICAL MATERIAL (PCT Rule 13bis)

A. The indications made below relate to the deposited microorganism or other biological material referred to in the description on page 15, line 37.

B. IDENTIFICATION OF DEPOSIT — Further deposits are identified on an additional sheet [X]

Name of depositary institution
Deutsche Sammlung von Mikroorganismen und Zellkulturen (DSMZ)

Address of depositary institution (including postal code and country)
Inhoffenstr. 7B
38124 Braunschweig
DE

| Date of deposit | Accession Number |
|---|---|
| 2007-09-07 | DSM ACC2858 |

C. ADDITIONAL INDICATIONS (leave blank if not applicable)  This information is continued on an additional sheet [X]

D. DESIGNATED STATES FOR WHICH INDICATIONS ARE MADE (if the indications are not for all designated States)

E. SEPARATE FURNISHING OF INDICATIONS (leave blank if not applicable)

The indications listed below will be submitted to the International Bureau later (specify the general nature of the indications e.g., "Accession Number of Deposit")

— For receiving Office use only —
[ ] This sheet was received with the international application
Authorized officer — For International Bureau use only —
[ ] This sheet was received by the International Bureau on:
Authorized officer Form PCT/RO/134 (July1998; reprint January 2004)

Additional Indications According to Form PCT/RO/134 for Accession Number DSM ACC2858:

Applicant herewith requests for those countries which have a respective provision that the furnishing of a sample of the deposited material referred to in the application may only be made to an independent, nominated expert (request of the "expert solution" where applicable, in particular in Australia, Canada, Croatia, Denmark, Finland, Germany, Iceland, Norway, Singapore, Spain, Sweden, United Kingdom, Europe).

For Europe, applicant accordingly requests that a sample of the deposited biological material will be made available as provided in Rule 33(1)(2) EPC until the publication of the mention of the grant of the patent or for 20 years from the date of filing if the application is refused or withdrawn or deemed to be withdrawn, only by the issue of a sample to an expert nominated by the person requesting the sample (Rule 32 EPC).

BUDAPEST TREATY ON THE INTERNATIONAL
RECOGNITION OF THE DEPOSIT OF MICROORGANISMS
FOR THE PURPOSES OF PATENT PROCEDURE
INTERNATIONAL FORM
Glycotope GmbH
Robert-Rössle-Str. 10
13125 Berlin
RECEIPT IN THE CASE OF AN ORIGINAL DEPOSIT
issued pursuant to Rule 7.1 by the
INTERNATIONAL DEPOSITARY AUTHORITY
identified at the bottom of this page

The invention claimed is:

1. An antibody or fragment or derivative thereof which is capable of binding to a mucin protein, wherein the antibody comprises at least a portion of a heavy chain variable region comprising a proline residue at amino acid position 28 according to the Kabat numbering; wherein the antibody or fragment or derivative thereof specifically binds the glycosylated MUC1 tumor epitope, and (a) comprises a heavy chain variable region comprising the amino acid sequence of SEQ ID NO: 16 and a light chain variable region comprising the amino acid sequence of SEQ ID NO: 28; or (b) comprises a heavy chain variable region comprising a
  (i) CDR1 comprising the amino acid sequence of SEQ ID NO: 1,
  (ii) CDR2 comprising the amino acid sequence of SEQ ID NO: 3, and
  (iii) CDR3 comprising the amino acid sequence of SEQ ID NO: 5; and
a light chain variable region comprising a
  (i) CDR1 comprising the amino acid sequence of SEQ ID NO: 17,
  (ii) CDR2 comprising the amino acid sequence of SEQ ID NO: 19, and
  (iii) CDR3 comprising the amino acid sequence of SEQ ID NO: 21.

2. The antibody or fragment or derivative thereof according to claim 1, wherein the antibody or fragment or derivative is capable of binding to the glycosylated MUC1 tumor epitope with a lower dissociation constant than a fragment or derivative of an antibody which is identical to the functional fragment or derivative, except that it does not comprise a proline residue at position 28, according to the Kabat numbering, of the heavy chain variable region.

3. The antibody or fragment or derivative thereof according to claim 1, having one or more of the following characteristics:

(a) the specific binding to its epitope is dependent on the conformation or the glycosylation pattern of the epitope;

(b) it is capable of specifically binding a peptide comprising the amino acid sequence PDTR, which is glycosylated at the threonine residue with N-acetyl galactosamine (Tn) or galactose β1-3 N-acetyl galactosamine (TF);

(c) it is capable of specifically binding to MUC1, in particular to at least a portion of the glycosylated extracellular tandem repeats of tumor-derived MUC1;

(d) it specifically binds the glycosylated MUC1 tumor epitope such that the strength of the bond is increased at least by a factor 20 in comparison with the bond to the non-glycosylated peptide of identical length and identical peptide sequence;
(e) it is engineered, preferably humanized;
(f) it comprises the antibody framework regions selected from the following:
(i) FRH1, FRH2, FRH3 and FRH4 for the variable heavy chain VH having the following amino acid sequences, the amino acid position corresponding to the numeration according to Kabat:

| Pos. | Amino |
|---|---|
| for FRH1 (SEQ ID NO: 7) | |
| 1 | E |
| 2 | V |
| 3 | Q or K |
| 4 | L |
| 5 | V |
| 6 | E |
| 7 | S |
| 8 | G |
| 9 | G |
| 10 | G |
| 11 | L |
| 12 | V |
| 13 | Q |
| 14 | P |
| 15 | G |
| 16 | G |
| 17 | S |
| 18 | L or M |
| 19 | R |
| 20 | L |
| 21 | S |
| 22 | C |
| 23 | A or V |
| 24 | A |
| 25 | S |
| 26 | G |
| 27 | F |
| 28 | P |
| 29 | F |
| 30 | S |
| for FRH2 (SEQ ID NO: 9) | |
| 36 | W |
| 37 | V |
| 38 | R |
| 39 | Q |
| 40 | A or S |
| 41 | P |
| 42 | G or E |
| 43 | K |
| 44 | G |
| 45 | L |
| 46 | E |
| 47 | W |
| 48 | V |
| 49 | G or A |
| for FRH3 (SEQ ID NO: 11) | |
| 66 | R |
| 67 | F |
| 68 | T |
| 69 | I |
| 70 | S |
| 71 | R |
| 72 | D |
| 73 | D |
| 74 | S |
| 75 | K |
| 76 | N or S |
| 77 | S |
| 78 | L or V |
| 79 | Y |
| 80 | L |
| 81 | Q |
| 82 | M |
| 82a | N |
| 82b | S |
| 82c | L |
| 83 | K |
| 84 | T |
| 85 | E |
| 86 | D |
| 87 | T |
| 88 | A |
| 89 | V |
| 90 | Y |
| 91 | Y |
| 92 | C |
| 93 | T or A |
| 94 | R |
| for FRH4 (SEQ ID NO: 13) | |
| 103 | W |
| 104 | G |
| 105 | Q |
| 106 | G |
| 107 | T |
| 108 | L |
| 109 | V or L |
| 110 | T |
| 111 | V |
| 112 | S |
| 113 | S |

(g) it comprises a framework region 1 comprising the amino acid sequence of SEQ ID NO: 7;
(h) it comprises a heavy chain variable region comprising the amino acid sequence of SEQ ID NO:15;
(i) it comprises a light chain variable region comprising the amino acid sequence of SEQ ID NO: 27;
(j) it shows cross-specificity with the antibody Pankomab comprising heavy and light chain variable region sequences comprising the amino acid sequences of SEQ ID NO: 29 and SEQ ID NO: 30.

4. A composition comprising the antibody or fragment or derivative thereof according to claim 1.

5. The composition according to claim 4 further comprising one or more components selected from the group consisting of solvents, diluents, and excipients.

6. The antibody or fragment or derivative thereof according to claim 1, having a glycosylation pattern which has one or more of the following characteristics:
(a) it is a human glycosylation pattern;
(b) it enhances the activity of the antibody, in particular its binding affinity to its specific epitope, its binding affinity to one or more of its downstream receptors such as Fc receptors, its complement dependent cytotoxicity (CDC), and/or its antibody-dependent cell-mediated cytotoxicity (ADCC);
(c) it is a glycosylation pattern as obtained when expressing the antibody or fragment or derivative thereof in a cell line selected from the group consisting of K562, KG1, MUTZ-3, NM-F9 [DSM ACC2606], NM-D4 [DSM ACC2605], NM-H9D8 [DSM ACC 2806], NM-H9D8-E6 [DSM ACC 2807], NM H9D8-E6Q12 [DSM ACC 2856], and GT-2X [DSM ACC 2858].

7. The antibody or fragment or derivative thereof according to claim 3, wherein the antibody or fragment or derivative comprises a framework region 1 comprising the amino acid sequence of SEQ ID NO: 8.

8. The antibody or fragment or derivative thereof according to claim 3, wherein the antibody or fragment or derivative comprises a heavy chain variable region comprising the amino acid sequence of SEQ ID NO: 16.

9. The antibody or fragment or derivative thereof according to claim 8, wherein the antibody or fragment or derivative comprises a light chain variable region comprising the amino acid sequence of SEQ ID NO: 28.

10. The antibody or fragment or derivative thereof according to claim 3, wherein the FRL1, FRL2, FRL3 and FRL4 for the light chain variable region VL have the following amino acid sequences, the amino acid position corresponding to the numeration according to Kabat:

| Pos. | Amino |
|---|---|
| for FRL1 (SEQ ID NO: 23) | |
| 1 | D |
| 2 | I |
| 3 | V |
| 4 | M |
| 5 | T |
| 6 | Q |
| 7 | S |
| 8 | P |
| 9 | L |
| 10 | S |
| 11 | L or N |
| 12 | P |
| 13 | V |
| 14 | T |
| 15 | P |
| 16 | G |
| 17 | E or D |
| 18 | P |
| 19 | A |
| 20 | S |
| 21 | I |
| 22 | S |
| 23 | C |
| for FRL2 (SEQ ID NO: 24) | |
| 35 | W |
| 36 | Y |
| 37 | L |
| 38 | Q |
| 39 | K |
| 40 | P |
| 41 | G |
| 42 | Q |
| 43 | S |
| 44 | P |
| 45 | Q |
| 46 | L |
| 47 | L |
| 48 | I |
| 49 | Y |
| for FRL3 (SEQ ID NO: 25) | |
| 57 | G |
| 58 | V |
| 59 | P |
| 60 | D |
| 61 | R |
| 62 | F |
| 63 | S |
| 64 | G |
| 65 | S |
| 66 | G |
| 67 | S |
| 68 | G |
| 69 | T |
| 70 | D |
| 71 | F |
| 72 | T |
| 73 | L |
| 74 | K or R |
| 75 | I |
| 76 | S |
| 77 | R |
| 78 | V |
| 79 | E |
| 80 | A |
| 81 | E |
| 82 | D |
| 83 | V |
| 84 | G |
| 85 | V |
| 86 | Y |
| 87 | Y |
| 88 | C |
| for FRL4 (SEQ ID NO: 26) | |
| 98 | F |
| 99 | G |
| 100 | Q or G |
| 101 | G |
| 102 | T |
| 103 | K |
| 104 | V |
| 105 | E |
| 106 | I |
| 107 | K |
| 108 | R. |

11. The antibody or fragment or derivative thereof according to claim 1, wherein the fragment or derivative of the antibody is selected from the group consisting of
(i) Fab fragments, monovalent fragments consisting of the variable region and the first constant domain of each the heavy and the light chain;
(ii) F(ab)₂ fragments, bivalent fragments comprising two Fab fragments linked by a disulfide bridge at the hinge region;
(iii) Fv fragments consisting of the heavy chain and light chain variable region of a single arm of an antibody;
(iv) scFv fragments, Fv fragments consisting of a single polypeptide chain;
(v) (Fv)₂ fragments consisting of two Fv fragments covalently linked together; and
(vi) multibodies consisting of a heavy chain variable region and a light chain variable region covalently linked together in such a manner that association of the heavy chain and light chain variable regions can only occur intermolecular but not intramolecular.

12. The antibody or fragment or derivative thereof according to claim 1, having an isotype selected from the group consisting of IgG, IgM, IgA, IgE and IgD.

13. A conjugate consisting of the antibody or fragment or derivative thereof according to claim 1 coupled to a further agent.

14. The conjugate according to claim 13, wherein the further agent is selected from the group consisting of antibodies or fragments of antibodies, enzymes, interaction domains, stabilizing domains, signaling sequences, detectable labels, fluorescent dyes, toxins, catalytic antibodies, cytolytic components, immunomodulators, immunoeffectors, MHC class I or class II antigens, chelators for radioactive labeling, radioisotopes, liposomes, transmembrane domains, viruses, cells, agents capable of killing cancer cells, radionuclides and cytotoxins.

15. A method of treating a cancer expressing MUC1 in a patient, comprising administering to the patient the antibody or fragment or derivative thereof according to claim 1.

16. The method according to claim 15, wherein the cancer is selected from the group consisting of leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer.

17. A method of treating a cancer expressing MUC1 in a patient, comprising administering to the patient the conjugate according to claim 13.

18. The method according to claim 17, wherein the cancer is selected from the group consisting of leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer.

* * * * *

SEQUENCE LISTING

<160> NUMBER OF SEQ ID NOS: 54

<210> SEQ ID NO 1
<211> LENGTH: 5
<212> TYPE: PRT
<213> ORGANISM: Artificial
<220> FEATURE:
<223> OTHER INFORMATION: CDR H1

<400> SEQUENCE: 1

Asn Tyr Trp Met Asn
1               5

<210> SEQ ID NO 2
<211> LENGTH: 5
<212> TYPE: PRT
<213> ORGANISM: Artificial
<220> FEATURE:
<223> OTHER INFORMATION: CDR H1

<400> SEQUENCE: 2

Asp Ala Trp Met Asp
1               5

<210> SEQ ID NO 3
<211> LENGTH: 19
<212> TYPE: PRT
<213> ORGANISM: Artificial
<220> FEATURE:
<223> OTHER INFORMATION: CDR H2

<400> SEQUENCE: 3

Glu Ile Arg Leu Lys Ser Asn Asn Tyr Thr Thr His Tyr Ala Glu Ser
1               5                   10                  15

Val Lys Gly

<210> SEQ ID NO 4
<211> LENGTH: 19
<212> TYPE: PRT
<213> ORGANISM: Artificial
<220> FEATURE:
<223> OTHER INFORMATION: CDR H2

<400> SEQUENCE: 4

Glu Ile Arg Ser Lys Ala Asn Asn His Ala Thr Tyr Tyr Ala Glu Ser
1               5                   10                  15

Val Lys Gly

<210> SEQ ID NO 5
<211> LENGTH: 6
<212> TYPE: PRT
<213> ORGANISM: Artificial
<220> FEATURE:
<223> OTHER INFORMATION: CDR H3

<400> SEQUENCE: 5

His Tyr Tyr Phe Asp Tyr
1               5

<210> SEQ ID NO 6
<211> LENGTH: 7
<212> TYPE: PRT
<213> ORGANISM: Artificial
<220> FEATURE:
<223> OTHER INFORMATION: CDR H3

<400> SEQUENCE: 6

Gly Gly Tyr Gly Phe Asp Tyr
1               5

<210> SEQ ID NO 7
<211> LENGTH: 30
<212> TYPE: PRT
<213> ORGANISM: Artificial
<220> FEATURE:
<223> OTHER INFORMATION: FR H1
<220> FEATURE:
<221> NAME/KEY: MISC_FEATURE
<222> LOCATION: (3)..(3)
<223> OTHER INFORMATION: Xaa is Gln or Lys
<220> FEATURE:
<221> NAME/KEY: MISC_FEATURE
<222> LOCATION: (18)..(18)
<223> OTHER INFORMATION: Xaa is Leu or Met
<220> FEATURE:
<221> NAME/KEY: MISC_FEATURE
<222> LOCATION: (23)..(23)
<223> OTHER INFORMATION: Xaa is Ala or Val

<400> SEQUENCE: 7

Glu Val Xaa Leu Val Glu Ser Gly Gly Gly Leu Val Gln Pro Gly Gly
1               5                   10                  15

Ser Xaa Arg Leu Ser Cys Xaa Ala Ser Gly Phe Pro Phe Ser
            20                  25                  30

<210> SEQ ID NO 8
<211> LENGTH: 30
<212> TYPE: PRT
<213> ORGANISM: Artificial
<220> FEATURE:
<223> OTHER INFORMATION: FR H1

<400> SEQUENCE: 8

Glu Val Gln Leu Val Glu Ser Gly Gly Gly Leu Val Gln Pro Gly Gly
1               5                   10                  15

Ser Met Arg Leu Ser Cys Val Ala Ser Gly Phe Pro Phe Ser
            20                  25                  30

<210> SEQ ID NO 9
<211> LENGTH: 14
<212> TYPE: PRT
<213> ORGANISM: Artificial
<220> FEATURE:
<223> OTHER INFORMATION: FR H2
<220> FEATURE:
<221> NAME/KEY: MISC_FEATURE
<222> LOCATION: (5)..(5)
<223> OTHER INFORMATION: Xaa is Ala or Ser
<220> FEATURE:
<221> NAME/KEY: MISC_FEATURE
<222> LOCATION: (7)..(7)
<223> OTHER INFORMATION: Xaa is Gly or Glu
<220> FEATURE:
<221> NAME/KEY: MISC_FEATURE
<222> LOCATION: (14)..(14)
<223> OTHER INFORMATION: Xaa is Gly or Ala

<400> SEQUENCE: 9

Trp Val Arg Gln Xaa Pro Xaa Lys Gly Leu Glu Trp Val Xaa
1               5                   10

<210> SEQ ID NO 10
<211> LENGTH: 14
<212> TYPE: PRT
<213> ORGANISM: Artificial

```
<220> FEATURE:
<223> OTHER INFORMATION: FR H2

<400> SEQUENCE: 10

Trp Val Arg Gln Ala Pro Gly Lys Gly Leu Glu Trp Val Gly
1               5                   10

<210> SEQ ID NO 11
<211> LENGTH: 32
<212> TYPE: PRT
<213> ORGANISM: Artificial
<220> FEATURE:
<223> OTHER INFORMATION: FR H3
<220> FEATURE:
<221> NAME/KEY: MISC_FEATURE
<222> LOCATION: (11)..(11)
<223> OTHER INFORMATION: Xaa is Asn or Ser
<220> FEATURE:
<221> NAME/KEY: MISC_FEATURE
<222> LOCATION: (13)..(13)
<223> OTHER INFORMATION: Xaa is Leu or Val
<220> FEATURE:
<221> NAME/KEY: MISC_FEATURE
<222> LOCATION: (31)..(31)
<223> OTHER INFORMATION: Xaa is Thr or Ala

<400> SEQUENCE: 11

Arg Phe Thr Ile Ser Arg Asp Asp Ser Lys Xaa Ser Xaa Tyr Leu Gln
1               5                   10                  15

Met Asn Ser Leu Lys Thr Glu Asp Thr Ala Val Tyr Tyr Cys Xaa Arg
            20                  25                  30

<210> SEQ ID NO 12
<211> LENGTH: 32
<212> TYPE: PRT
<213> ORGANISM: Artificial
<220> FEATURE:
<223> OTHER INFORMATION: FR H3

<400> SEQUENCE: 12

Arg Phe Thr Ile Ser Arg Asp Asp Ser Lys Asn Ser Leu Tyr Leu Gln
1               5                   10                  15

Met Asn Ser Leu Lys Thr Glu Asp Thr Ala Val Tyr Tyr Cys Thr Arg
            20                  25                  30

<210> SEQ ID NO 13
<211> LENGTH: 11
<212> TYPE: PRT
<213> ORGANISM: Artificial
<220> FEATURE:
<223> OTHER INFORMATION: FR H4
<220> FEATURE:
<221> NAME/KEY: MISC_FEATURE
<222> LOCATION: (7)..(7)
<223> OTHER INFORMATION: Xaa is Val or Leu

<400> SEQUENCE: 13

Trp Gly Gln Gly Thr Leu Xaa Thr Val Ser Ser
1               5                   10

<210> SEQ ID NO 14
<211> LENGTH: 11
<212> TYPE: PRT
<213> ORGANISM: Artificial
<220> FEATURE:
<223> OTHER INFORMATION: FR H4

<400> SEQUENCE: 14
```

Trp Gly Gln Gly Thr Leu Val Thr Val Ser Ser
1               5                   10

<210> SEQ ID NO 15
<211> LENGTH: 117
<212> TYPE: PRT
<213> ORGANISM: Artificial
<220> FEATURE:
<223> OTHER INFORMATION: heavy chain variable region
<220> FEATURE:
<221> NAME/KEY: MISC_FEATURE
<222> LOCATION: (3)..(3)
<223> OTHER INFORMATION: Xaa is Gln or Lys
<220> FEATURE:
<221> NAME/KEY: MISC_FEATURE
<222> LOCATION: (18)..(18)
<223> OTHER INFORMATION: Xaa is Leu or Met
<220> FEATURE:
<221> NAME/KEY: MISC_FEATURE
<222> LOCATION: (23)..(23)
<223> OTHER INFORMATION: Xaa is Ala or Val
<220> FEATURE:
<221> NAME/KEY: MISC_FEATURE
<222> LOCATION: (40)..(40)
<223> OTHER INFORMATION: Xaa is Ala or Ser
<220> FEATURE:
<221> NAME/KEY: MISC_FEATURE
<222> LOCATION: (42)..(42)
<223> OTHER INFORMATION: Xaa is Gly or Glu
<220> FEATURE:
<221> NAME/KEY: MISC_FEATURE
<222> LOCATION: (49)..(49)
<223> OTHER INFORMATION: Xaa is Gly or Ala
<220> FEATURE:
<221> NAME/KEY: MISC_FEATURE
<222> LOCATION: (79)..(79)
<223> OTHER INFORMATION: Xaa is Asn or Ser
<220> FEATURE:
<221> NAME/KEY: MISC_FEATURE
<222> LOCATION: (81)..(81)
<223> OTHER INFORMATION: Xaa is Leu or Val
<220> FEATURE:
<221> NAME/KEY: MISC_FEATURE
<222> LOCATION: (99)..(99)
<223> OTHER INFORMATION: Xaa is Thr or Ala
<220> FEATURE:
<221> NAME/KEY: MISC_FEATURE
<222> LOCATION: (113)..(113)
<223> OTHER INFORMATION: Xaa is Val or Leu

<400> SEQUENCE: 15

Glu Val Xaa Leu Val Glu Ser Gly Gly Gly Leu Val Gln Pro Gly Gly
1               5                   10                  15

Ser Xaa Arg Leu Ser Cys Xaa Ala Ser Gly Phe Pro Phe Ser Asn Tyr
            20                  25                  30

Trp Met Asn Trp Val Arg Gln Xaa Pro Xaa Lys Gly Leu Glu Trp Val
        35                  40                  45

Xaa Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Xaa Ser
65                  70                  75                  80

Xaa Tyr Leu Gln Met Asn Ser Leu Lys Thr Glu Asp Thr Ala Val Tyr
                85                  90                  95

Tyr Cys Xaa Arg His Tyr Tyr Phe Asp Tyr Trp Gly Gln Gly Thr Leu
            100                 105                 110

Xaa Thr Val Ser Ser
        115

<210> SEQ ID NO 16

```
<211> LENGTH: 117
<212> TYPE: PRT
<213> ORGANISM: Artificial
<220> FEATURE:
<223> OTHER INFORMATION: heavy chain variable region

<400> SEQUENCE: 16

Glu Val Gln Leu Val Glu Ser Gly Gly Gly Leu Val Gln Pro Gly Gly
1               5                   10                  15

Ser Met Arg Leu Ser Cys Val Ala Ser Gly Phe Pro Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
        115

<210> SEQ ID NO 17
<211> LENGTH: 16
<212> TYPE: PRT
<213> ORGANISM: Artificial
<220> FEATURE:
<223> OTHER INFORMATION: CDR L1

<400> SEQUENCE: 17

Arg Ser Ser Lys Ser Leu Leu His Ser Asn Gly Ile Thr Tyr Phe Phe
1               5                   10                  15

<210> SEQ ID NO 18
<211> LENGTH: 16
<212> TYPE: PRT
<213> ORGANISM: Artificial
<220> FEATURE:
<223> OTHER INFORMATION: CDR L1

<400> SEQUENCE: 18

Arg Ser Ser Gln Ser Ile Val His Ser Asn Gly Asn Thr Tyr Leu Glu
1               5                   10                  15

<210> SEQ ID NO 19
<211> LENGTH: 7
<212> TYPE: PRT
<213> ORGANISM: Artificial
<220> FEATURE:
<223> OTHER INFORMATION: CDR L2

<400> SEQUENCE: 19

Gln Met Ser Asn Leu Ala Ser
1               5

<210> SEQ ID NO 20
<211> LENGTH: 7
<212> TYPE: PRT
<213> ORGANISM: Artificial
<220> FEATURE:
<223> OTHER INFORMATION: CDR L2
```

```
<400> SEQUENCE: 20

Lys Val Ser Asn Arg Phe Ser
1               5

<210> SEQ ID NO 21
<211> LENGTH: 9
<212> TYPE: PRT
<213> ORGANISM: Artificial
<220> FEATURE:
<223> OTHER INFORMATION: CDR L3

<400> SEQUENCE: 21

Ala Gln Asn Leu Glu Leu Pro Pro Thr
1               5

<210> SEQ ID NO 22
<211> LENGTH: 9
<212> TYPE: PRT
<213> ORGANISM: Artificial
<220> FEATURE:
<223> OTHER INFORMATION: CDR L3

<400> SEQUENCE: 22

Phe Gln Gly Ser His Val Pro Leu Thr
1               5

<210> SEQ ID NO 23
<211> LENGTH: 23
<212> TYPE: PRT
<213> ORGANISM: Artificial
<220> FEATURE:
<223> OTHER INFORMATION: FR L1
<220> FEATURE:
<221> NAME/KEY: MISC_FEATURE
<222> LOCATION: (11)..(11)
<223> OTHER INFORMATION: Xaa is Leu or Asn
<220> FEATURE:
<221> NAME/KEY: MISC_FEATURE
<222> LOCATION: (17)..(17)
<223> OTHER INFORMATION: Xaa is Glu or Asp

<400> SEQUENCE: 23

Asp Ile Val Met Thr Gln Ser Pro Leu Ser Xaa Pro Val Thr Pro Gly
1               5                   10                  15

Xaa Pro Ala Ser Ile Ser Cys
            20

<210> SEQ ID NO 24
<211> LENGTH: 15
<212> TYPE: PRT
<213> ORGANISM: Artificial
<220> FEATURE:
<223> OTHER INFORMATION: FR L2

<400> SEQUENCE: 24

Trp Tyr Leu Gln Lys Pro Gly Gln Ser Pro Gln Leu Leu Ile Tyr
1               5                   10                  15

<210> SEQ ID NO 25
<211> LENGTH: 32
<212> TYPE: PRT
<213> ORGANISM: Artificial
<220> FEATURE:
<223> OTHER INFORMATION: FR L3
<220> FEATURE:
<221> NAME/KEY: MISC_FEATURE
<222> LOCATION: (18)..(18)
<223> OTHER INFORMATION: Xaa is Lys or Arg
```

```
<400> SEQUENCE: 25

Gly Val Pro Asp Arg Phe Ser Gly Ser Gly Ser Gly Thr Asp Phe Thr
1               5                   10                  15

Leu Xaa Ile Ser Arg Val Glu Ala Glu Asp Val Gly Val Tyr Tyr Cys
            20                  25                  30

<210> SEQ ID NO 26
<211> LENGTH: 12
<212> TYPE: PRT
<213> ORGANISM: Artificial
<220> FEATURE:
<223> OTHER INFORMATION: FR L4
<220> FEATURE:
<221> NAME/KEY: MISC_FEATURE
<222> LOCATION: (3)..(3)
<223> OTHER INFORMATION: Xaa is Gln or Gly

<400> SEQUENCE: 26

Phe Gly Xaa Gly Thr Lys Val Glu Ile Lys Arg Ala
1               5                   10

<210> SEQ ID NO 27
<211> LENGTH: 114
<212> TYPE: PRT
<213> ORGANISM: Artificial
<220> FEATURE:
<223> OTHER INFORMATION: light chain variable region
<220> FEATURE:
<221> NAME/KEY: MISC_FEATURE
<222> LOCATION: (11)..(11)
<223> OTHER INFORMATION: Xaa is Leu or Asn
<220> FEATURE:
<221> NAME/KEY: MISC_FEATURE
<222> LOCATION: (17)..(17)
<223> OTHER INFORMATION: Xaa is Glu or Asp
<220> FEATURE:
<221> NAME/KEY: MISC_FEATURE
<222> LOCATION: (79)..(79)
<223> OTHER INFORMATION: Xaa is Lys or Arg
<220> FEATURE:
<221> NAME/KEY: MISC_FEATURE
<222> LOCATION: (105)..(105)
<223> OTHER INFORMATION: Xaa is Gln or Gly

<400> SEQUENCE: 27

Asp Ile Val Met Thr Gln Ser Pro Leu Ser Xaa Pro Val Thr Pro Gly
1               5                   10                  15

Xaa Pro Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Xaa Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Xaa Gly Thr Lys Val Glu Ile Lys
            100                 105                 110

Arg Ala

<210> SEQ ID NO 28
<211> LENGTH: 114
<212> TYPE: PRT
```

<213> ORGANISM: Artificial
<220> FEATURE:
<223> OTHER INFORMATION: light chain vatiable region

<400> SEQUENCE: 28

Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gln Gly Thr Lys Val Glu Ile Lys
            100                 105                 110

Arg Ala

<210> SEQ ID NO 29
<211> LENGTH: 117
<212> TYPE: PRT
<213> ORGANISM: Mus musculus

<400> SEQUENCE: 29

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Ser
        115

<210> SEQ ID NO 30
<211> LENGTH: 114
<212> TYPE: PRT
<213> ORGANISM: Mus musculus

<400> SEQUENCE: 30

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro

-continued

```
                    50                  55                  60
Asp Arg Phe Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                 85                  90                  95

Leu Glu Leu Pro Pro Thr Phe Gly Gly Gly Thr Lys Leu Glu Ile Lys
                100                 105                 110

Arg Ala

<210> SEQ ID NO 31
<211> LENGTH: 446
<212> TYPE: PRT
<213> ORGANISM: Artificial
<220> FEATURE:
<223> OTHER INFORMATION: heavy chain of a humanized antibody

<400> SEQUENCE: 31

Glu Val Gln Leu Val Glu Ser Gly Gly Gly Leu Val Gln Pro Gly Gly
  1               5                  10                  15

Ser Met Arg Leu Ser Cys Val Ala Ser Gly Phe Pro Phe Ser Asn Tyr
                 20                  25                  30

Trp Met Asn Trp Val Arg Gln Ala Pro Gly Lys Gly Leu Glu Trp Val
             35                  40                  45

Gly Glu Ile Arg Leu Lys Ser Asn Asn Tyr Thr Thr His Tyr Ala Glu
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Thr Arg His Tyr Tyr Phe Asp Tyr Trp Gly Gln Gly Thr Leu
                100                 105                 110

Val Thr Val Ser Gly Ser Thr Lys Gly Pro Ser Val Phe Pro Leu Ala
             115                 120                 125

Pro Ser Ser Lys Ser Thr Ser Gly Gly Thr Ala Ala Leu Gly Cys Leu
130                 135                 140

Val Lys Asp Tyr Phe Pro Glu Pro Val Thr Val Ser Asn Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
        210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

```
Leu Thr Val Leu His Gln Asp Trp Leu Asn Gly Lys Glu Tyr Lys Gly
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Asp Glu Leu Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 32
<211> LENGTH: 219
<212> TYPE: PRT
<213> ORGANISM: Artificial
<220> FEATURE:
<223> OTHER INFORMATION: light chain of a humanized antibody

<400> SEQUENCE: 32

Asp Ile Val Met Thr Gln Ser Pro Leu Ser Asn Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 33
<211> LENGTH: 30
<212> TYPE: PRT
<213> ORGANISM: Artificial
<220> FEATURE:
<223> OTHER INFORMATION: FR H1
<220> FEATURE:
<221> NAME/KEY: MISC_FEATURE
<222> LOCATION: (3)..(3)
<223> OTHER INFORMATION: Xaa is Gln or Lys
<220> FEATURE:
<221> NAME/KEY: MISC_FEATURE
<222> LOCATION: (18)..(18)
<223> OTHER INFORMATION: Xaa is Leu or Met
<220> FEATURE:
<221> NAME/KEY: MISC_FEATURE
<222> LOCATION: (23)..(23)
<223> OTHER INFORMATION: Xaa is Ala or Val

<400> SEQUENCE: 33

Glu Val Xaa Leu Val Glu Ser Gly Gly Gly Leu Val Gln Pro Gly Gly
1               5                   10                  15

Ser Xaa Arg Leu Ser Cys Xaa Ala Ser Gly Phe Thr Phe Ser
            20                  25                  30

<210> SEQ ID NO 34
<211> LENGTH: 30
<212> TYPE: PRT
<213> ORGANISM: Artificial
<220> FEATURE:
<223> OTHER INFORMATION: FR H1

<400> SEQUENCE: 34

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser
            20                  25                  30

<210> SEQ ID NO 35
<211> LENGTH: 14
<212> TYPE: PRT
<213> ORGANISM: Artificial
<220> FEATURE:
<223> OTHER INFORMATION: FR H2

<400> SEQUENCE: 35

Trp Val Arg Gln Ser Pro Glu Lys Gly Leu Glu Trp Val Ala
1               5                   10

<210> SEQ ID NO 36
<211> LENGTH: 32
<212> TYPE: PRT
<213> ORGANISM: Artificial
<220> FEATURE:
<223> OTHER INFORMATION: FR H3

<400> SEQUENCE: 36

Arg Phe Thr Ile Ser Arg Asp Asp Ser Lys Ser Ser Val Ser Leu Gln
1               5                   10                  15

Met Asn Asn Leu Arg Val Glu Asp Thr Gly Ile Tyr Tyr Cys Thr Arg
            20                  25                  30

<210> SEQ ID NO 37
<211> LENGTH: 11
<212> TYPE: PRT
<213> ORGANISM: Artificial

<220> FEATURE:
<223> OTHER INFORMATION: FR H4

<400> SEQUENCE: 37

Trp Gly Gln Gly Thr Thr Leu Thr Val Ser Ser
1               5                   10

<210> SEQ ID NO 38
<211> LENGTH: 117
<212> TYPE: PRT
<213> ORGANISM: Artificial
<220> FEATURE:
<223> OTHER INFORMATION: heavy chain variable region

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
        115

<210> SEQ ID NO 39
<211> LENGTH: 446
<212> TYPE: PRT
<213> ORGANISM: Artificial
<220> FEATURE:
<223> OTHER INFORMATION: heavy chain of a humanized antibody

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Gly Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

```
Val Lys Asp Tyr Phe Pro Glu Pro Val Thr Val Ser Asn Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Gly
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 40
<211> LENGTH: 446
<212> TYPE: PRT
<213> ORGANISM: Artificial
<220> FEATURE:
<223> OTHER INFORMATION: heavy chain of a chimeric antibody

<400> SEQUENCE: 40

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
            35                  40                  45

Ala Glu Ile Arg Leu Lys Ser Asn Asn Tyr Thr Thr His Tyr Ala Glu
50                  55                  60
```

```
Ser Val Lys Gly Arg Phe Thr Ile Ser Arg Asp Asp Ser Lys Ser Ser
 65                  70                  75                  80

Val Ser Leu Gln Met Asn Asn Leu Arg Val Glu Asp Thr Gly Ile Tyr
                 85                  90                  95

Tyr Cys Thr Arg His Tyr Tyr Phe Asp Tyr Trp Gly Gln Gly Thr Thr
                100                 105                 110

Leu Thr Val Ser Gly Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Asn Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Gly
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 41
<211> LENGTH: 219
<212> TYPE: PRT
<213> ORGANISM: Artificial
<220> FEATURE:
<223> OTHER INFORMATION: light chain of a chimeric antibody
```

<400> SEQUENCE: 41

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 42
<211> LENGTH: 117
<212> TYPE: PRT
<213> ORGANISM: Artificial
<220> FEATURE:
<223> OTHER INFORMATION: heavy chain variable region

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
            115

```
<210> SEQ ID NO 43
<211> LENGTH: 117
<212> TYPE: PRT
<213> ORGANISM: Artificial
<220> FEATURE:
<223> OTHER INFORMATION: heavy chain variable region

<400> SEQUENCE: 43

Glu Val Gln Leu Val Glu Ser Gly Gly Gly Leu Val Gln Pro Gly Gly
1               5                   10                  15

Ser Met Arg Leu Ser Cys Val Ala Ser Gly Phe Thr Phe Ser Asn Tyr
            20                  25                  30

Trp Met Asn Trp Val Arg Gln Ala Pro Gly Lys Gly Leu Glu Trp Val
        35                  40                  45

Gly Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
        115

<210> SEQ ID NO 44
<211> LENGTH: 117
<212> TYPE: PRT
<213> ORGANISM: Artificial
<220> FEATURE:
<223> OTHER INFORMATION: heavy chain variable region

<400> SEQUENCE: 44

Glu Val Gln Leu Val Glu Ser Gly Gly Gly Leu Val Gln Pro Gly Gly
1               5                   10                  15

Ser Met Arg Leu Ser Cys Val Ala Ser Gly Phe Thr Phe Ser Asn Tyr
            20                  25                  30

Trp Met Asn Trp Val Arg Gln Ser Pro Gly Lys Gly Leu Glu Trp Val
        35                  40                  45

Gly Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
        115

<210> SEQ ID NO 45
<211> LENGTH: 117
<212> TYPE: PRT
<213> ORGANISM: Artificial
<220> FEATURE:
<223> OTHER INFORMATION: heavy chain variable region

<400> SEQUENCE: 45

Glu Val Gln Leu Val Glu Ser Gly Gly Gly Leu Val Gln Pro Gly Gly
```

```
            1               5                  10                  15
Ser Met Arg Leu Ser Cys Val Ala Ser Gly Phe Thr Phe Ser Asn Tyr
                20                  25                  30

Trp Met Asn Trp Val Arg Gln Ser Pro Glu Lys Gly Leu Glu Trp Val
            35                  40                  45

Gly Glu Ile Arg Leu Lys Ser Asn Asn Tyr Thr Thr His Tyr Ala Glu
        50                  55                  60

Ser Val Lys Gly Arg Phe Thr Ile Ser Arg Asp Asp Ser Lys Asn Ser
 65                 70                  75                  80

Leu Tyr Leu Gln Met Asn Ser Leu Lys Thr Glu Asp Thr Ala Val Tyr
                85                  90                  95

Tyr Cys Thr Arg His Tyr Tyr Phe Asp Tyr Trp Gly Gln Gly Thr Leu
            100                 105                 110

Val Thr Val Ser Ser
            115
```

<210> SEQ ID NO 46
<211> LENGTH: 114
<212> TYPE: PRT
<213> ORGANISM: Artificial
<220> FEATURE:
<223> OTHER INFORMATION: light chain variable region

<400> SEQUENCE: 46

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Gly Ile Thr Tyr Phe Phe Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Gly Ser Gly Ser Gly Thr Asp Phe Thr Leu Lys Ile
 65                 70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gln Gly Thr Lys Val Glu Ile Lys
            100                 105                 110

Arg Ala
```

<210> SEQ ID NO 47
<211> LENGTH: 114
<212> TYPE: PRT
<213> ORGANISM: Artificial
<220> FEATURE:
<223> OTHER INFORMATION: light chain variable region

<400> SEQUENCE: 47

```
Asp Ile Val Met Thr Gln Ser Pro Leu Ser Asn Pro Val Thr Pro Gly
 1               5                  10                  15

Glu Pro Ala Ser Ile Ser Cys Arg Ser Ser Lys Ser Leu Leu His Ser
                20                  25                  30

Asn Gly Ile Thr Tyr Leu Phe Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Ala Gln Asn
                    85                  90                  95

Leu Glu Leu Pro Pro Thr Phe Gly Gly Gly Thr Lys Val Glu Ile Lys
            100                 105                 110

Arg Ala

<210> SEQ ID NO 48
<211> LENGTH: 114
<212> TYPE: PRT
<213> ORGANISM: Artificial
<220> FEATURE:
<223> OTHER INFORMATION: light chain variable region

<400> SEQUENCE: 48

Asp Ile Val Met Thr Gln Ser Pro Leu Ser Asn Pro Val Thr Pro Gly
1               5                   10                  15

Asp Pro Ala Ser Ile Ser Cys Arg Ser Ser Lys Ser Leu Leu His Ser
            20                  25                  30

Asn Gly Ile Thr Tyr Leu Phe Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                    85                  90                  95

Leu Glu Leu Pro Pro Thr Phe Gly Gly Gly Thr Lys Val Glu Ile Lys
            100                 105                 110

Arg Ala

<210> SEQ ID NO 49
<211> LENGTH: 4
<212> TYPE: PRT
<213> ORGANISM: Artificial
<220> FEATURE:
<223> OTHER INFORMATION: epitope

<400> SEQUENCE: 49

Pro Asp Thr Arg
1

<210> SEQ ID NO 50
<211> LENGTH: 5
<212> TYPE: PRT
<213> ORGANISM: Artificial
<220> FEATURE:
<223> OTHER INFORMATION: epitope

<400> SEQUENCE: 50

Pro Asp Thr Arg Pro
1               5

<210> SEQ ID NO 51
<211> LENGTH: 30
<212> TYPE: PRT
<213> ORGANISM: Artificial
<220> FEATURE:
<223> OTHER INFORMATION: target peptide

<400> SEQUENCE: 51
```

```
Ala Pro Pro Ala His Gly Val Thr Ser Ala Pro Asp Thr Arg Pro Ala
1               5                   10                  15

Pro Gly Ser Thr Ala Pro Pro Ala His Gly Val Thr Ser Ala
            20                  25                  30
```

<210> SEQ ID NO 52
<211> LENGTH: 41
<212> TYPE: PRT
<213> ORGANISM: Artificial
<220> FEATURE:
<223> OTHER INFORMATION: target peptide
<220> FEATURE:
<221> NAME/KEY: CARBOHYD
<222> LOCATION: (10)..(10)
<223> OTHER INFORMATION: GalNAc alpha
<220> FEATURE:
<221> NAME/KEY: CARBOHYD
<222> LOCATION: (30)..(30)
<223> OTHER INFORMATION: GalNAc alpha

<400> SEQUENCE: 52

```
Ala His Gly Val Thr Ser Ala Pro Asp Thr Arg Pro Ala Pro Gly Ser
1               5                   10                  15

Thr Ala Pro Pro Ala His Gly Val Thr Ser Ala Pro Asp Thr Arg Pro
            20                  25                  30

Ala Pro Gly Ser Thr Ala Pro Pro Ala
            35                  40
```

<210> SEQ ID NO 53
<211> LENGTH: 81
<212> TYPE: PRT
<213> ORGANISM: Artificial
<220> FEATURE:
<223> OTHER INFORMATION: target peptide
<220> FEATURE:
<221> NAME/KEY: CARBOHYD
<222> LOCATION: (10)..(10)
<223> OTHER INFORMATION: GalNAc alpha
<220> FEATURE:
<221> NAME/KEY: CARBOHYD
<222> LOCATION: (30)..(30)
<223> OTHER INFORMATION: GalNAc alpha
<220> FEATURE:
<221> NAME/KEY: CARBOHYD
<222> LOCATION: (50)..(50)
<223> OTHER INFORMATION: GalNAc alpha
<220> FEATURE:
<221> NAME/KEY: CARBOHYD
<222> LOCATION: (70)..(70)
<223> OTHER INFORMATION: GalNAc alpha

<400> SEQUENCE: 53

```
Ala His Gly Val Thr Ser Ala Pro Asp Thr Arg Pro Ala Pro Gly Ser
1               5                   10                  15

Thr Ala Pro Pro Ala His Gly Val Thr Ser Ala Pro Asp Thr Arg Pro
            20                  25                  30

Ala Pro Gly Ser Thr Ala Pro Pro Ala His Gly Val Thr Ser Ala Pro
            35                  40                  45

Asp Thr Arg Pro Ala Pro Gly Ser Thr Ala Pro Pro Ala His Gly Val
    50                  55                  60

Thr Ser Ala Pro Asp Thr Arg Pro Ala Pro Gly Ser Thr Ala Pro Pro
65                  70                  75                  80

Ala
```

<210> SEQ ID NO 54
<211> LENGTH: 101

```
<212> TYPE: PRT
<213> ORGANISM: Artificial
<220> FEATURE:
<223> OTHER INFORMATION: target peptide
<220> FEATURE:
<221> NAME/KEY: CARBOHYD
<222> LOCATION: (10)..(10)
<223> OTHER INFORMATION: GalNAc alpha
<220> FEATURE:
<221> NAME/KEY: CARBOHYD
<222> LOCATION: (30)..(30)
<223> OTHER INFORMATION: GalNAc alpha
<220> FEATURE:
<221> NAME/KEY: CARBOHYD
<222> LOCATION: (50)..(50)
<223> OTHER INFORMATION: GalNAc alpha
<220> FEATURE:
<221> NAME/KEY: CARBOHYD
<222> LOCATION: (70)..(70)
<223> OTHER INFORMATION: GalNAc alpha
<220> FEATURE:
<221> NAME/KEY: CARBOHYD
<222> LOCATION: (90)..(90)
<223> OTHER INFORMATION: GalNAc alpha

<400> SEQUENCE: 54

Ala His Gly Val Thr Ser Ala Pro Asp Thr Arg Pro Ala Pro Gly Ser
 1               5                  10                  15

Thr Ala Pro Pro Ala His Gly Val Thr Ser Ala Pro Asp Thr Arg Pro
            20                  25                  30

Ala Pro Gly Ser Thr Ala Pro Pro Ala His Gly Val Thr Ser Ala Pro
        35                  40                  45

Asp Thr Arg Pro Ala Pro Gly Ser Thr Ala Pro Pro Ala His Gly Val
    50                  55                  60

Thr Ser Ala Pro Asp Thr Arg Pro Ala Pro Gly Ser Thr Ala Pro Pro
65                  70                  75                  80

Ala His Gly Val Thr Ser Ala Pro Asp Thr Arg Pro Ala Pro Gly Ser
                85                  90                  95

Thr Ala Pro Pro Ala
            100
```